US006210923B1

(12) United States Patent
Lee et al.

(10) Patent No.: US 6,210,923 B1
(45) Date of Patent: Apr. 3, 2001

(54) MAMMALIAN CIRCADIAN REGULATOR M-RIGUI2 (MPER2)

(75) Inventors: Cheng-Chi Lee; Urs Albrecht; Gregor Eichele; Zhong-Sheng Sun, all of Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/220,641

(22) Filed: Dec. 24, 1998

Related U.S. Application Data

(60) Provisional application No. 60/068,886, filed on Dec. 26, 1997.

(51) Int. Cl.$^7$ .......................... C12P 21/06; C07H 17/00; C07K 14/00

(52) U.S. Cl. .................... 435/69.1; 435/320.1; 435/325; 435/252.3; 435/348; 435/6; 536/23.1; 530/350

(58) Field of Search ................................ 435/69.1, 320.1, 435/252.3, 325, 348, 6; 536/23.1; 530/350

(56) References Cited

PUBLICATIONS

Citri et al., Nature 326:42–47, Mar. 1987.*

* cited by examiner

*Primary Examiner*—Karen Cochrane Carlson
(74) *Attorney, Agent, or Firm*—Benjamin Aaron Adler

(57) ABSTRACT

The present invention provides DNA encoding a m-rigui2 protein selected from the group consisting of: (a) isolated DNA which encodes a m-rigui2 protein; (b) isolated DNA which hybridizes to isolated DNA of (a) above and which encodes a m-rigui2 protein; and (c) isolated DNA differing from the isolated DNAs of (a) and (b) above in codon sequence due to the degeneracy of the genetic code, and which encodes a m-rigui2 protein. Also provided is a vector capable of expressing the DNA adapted for expression in a recombinant cell and regulatory elements necessary for expression of the DNA in the cell. Further, a host cell transfected with the vector disclosed herein the vector expressing a m-rigui2 protein.

11 Claims, 14 Drawing Sheets

(12 of 14 Drawing Sheet(s) Filed in Color)

MAMMALIAN CIRCADIAN REGULATOR M-RIGUI2 (MPER2)

This application claims benefit of priority of provisional application U.S. Serial No. 60/068,886, filed Dec. 26, 1997.

FEDERAL FUNDING LEGEND

This invention was created in part using funds from the federal government under DAMD 17-94-J-4484 from the Department of Defense. The U.S. government, therefore, has certain rights in this invention.

BACKGROUND OF THE INVENTION

1. Field of the Invention

The present invention relates generally to the fields of molecular genetics and the biology of circadian rhythms. More specifically, the present invention relates to characterization and squencing of the mammalian circadian regulator m-rigui2.

2. Description of the Related Art

That genes control circadian rhythms of higher organisms was first established in the fruit fly by Konopka and Benzer (1971), who demonstrated that certain point mutations in *Drosophila melanogaster* caused altered circadian rhythms. The mutated gene, period (per), was subsequently isolated (Bargiello et al., 1984) and was found to be expressed in a circadian pattern (Hardin et al., 1990). This finding, and similar data from bacteria, fungi, and plants, has led to the general idea that periodically expressed genes constitute the physiological basis of circadian clocks in all living organisms (Hall and Rosbash, 1993; Takahashi, 1995; Dunlap, 1996).

The circadian rhythm which controls the mammalian sleep/wake cycle is being investigated intensively. However, the molecular components that constitute this circadian clock and the cellular organization that sets the phase and pace of the circadian clock in mammals were, until very recently, virtually unknown. Extensive physiological and behavioral studies have established that the circadian clock is characterized by a cycle of approximately 24 hours in duration, which, presumably, reflects the periodicity by which the Earth rotates. When organisms are placed in darkness or constant light, this clock is self-sustaining, behaving as a pacemaker. The endogenous clock is further distinguished by its ability to be entrained to a new light/dark regime by environmental cues such as light and temperature cycles (Pittendrigh, 1993; Takahashi, 1995). For example, pulses of light or exposure to different time zones reset the clock.

Some of the proteins that control the circadian process in mammals may be related to those found in fruit flies (Hall, 1990; Siwicki et al., 1992). In Drosophila, per and timeless (tim) encode essential components of the circadian clock (Sehgal et al., 1994; Reppert and Sauman, 1995). A heterodimer of Per and Tim proteins may regulate the circadian process by creating a negative feedback loop controlling per and tim expression (Zeng et al., 1996). Two lines of evidence: the oscillatory nature of per expression and the phenotype of per mutants, indicate the central role of the per gene in the circadian machinery of insects (Konopka and Benzer, 1971; Citri et al., 1987; Hardin et al., 1990; Hall, 1996).

The circadian clock mechanism can be divided into three components: (1) the input signaling mechanisms, (2) a circadian pacemaker or clock, and (3) the output signaling mechanisms. The input involves the transmission of diurnal environmental cues such as light to the clock, primarily through the retinohypothalamic tract (Moore, 1995). The circadian pacemaker integrates external cues and initiates a variety of signals to the output pathway. In other words, the output pathway transmits the clock's rhythm to the body to evoke a variety of circadian behaviors such as the sleep-wake cycle. Despite the complex role played by the circadian pacemaker, it may consist of a limited number of components. It may be possible to identify such components either through genetic screens in mice (King et al., 1997) or through homology screens of libraries (Tei et al., 1997).

The recent identification of a human ortholog of Drosophila per has created opportunities to investigate the mammalian circadian clock. This gene was independently discovered by Sun et al. (1997) who named it RIGUI (after an ancient Chinese sundial) and by Tei et al. (1997) who named it h-per (because of sequence similarity with Drosophila per). The mouse homolog, m-rigui/m-per, is the first mammalian gene that meets the properties of a circadian regulator, such as circadian expression in the suprachiasmatic nucleus (SCN), self-sustained oscillation, and entrainment of circadian expression by external light cues. M-rigui1 and m-rigui2 are also known in the art as mPer1 and mPer2. Recently, a third homolog, known as mPer3, has been identified and characterized (Zylka, et al. 1998, Takumi et al, 1998)

The prior art is deficient in the lack of the characterization and squencing of the mammalian circadian regulator m-rigui2. The present invention fulfills this longstanding need and desire in the art.

SUMMARY OF THE INVENTION

In one embodiment of the present invention, there is provided DNA encoding a m-rigui2 protein selected from the group consisting of: (a) isolated DNA which encodes a m-rigui2 protein; (b) isolated DNA which hybridizes to isolated DNA of (a) above and which encodes a RIGUI m-rigui2; and (c) isolated DNA differing from the isolated DNAs of (a) and (b) above in codon sequence due to the degeneracy of the genetic code, and which encodes a m-rigui2 protein.

In another embodiment of the present invention, there is provided a vector capable of expressing the DNA disclosed herein adapted for expression in a recombinant cell and regulatory elements necessary for expression of the DNA in the cell.

In yet another embodiment of the present invention, there is provided an isolated and purified m-rigui2 protein coded for by DNA selected from the group consisting of: (a) isolated DNA which encodes a m-rigui2 protein; (b) isolated DNA which hybridizes to isolated DNA of (a) above and which encodes a m-rigui2 protein; and (c) isolated DNA differing from the isolated DNAs of (a) and (b) above in codon sequence due to the degeneracy of the genetic code, and which encodes a m-rigui2 protein.

In still yet another embodiment of the present invention, there is provided a method of detecting expression of the protein of the present invention, comprising the steps of: (a) contacting mRNA obtained from a cell with a labeled hybridization probe; and (b) detecting hybridization of the probe with the mRNA.

Other and further aspects, features, and advantages of the present invention will be apparent from the following description of the presently preferred embodiments of the invention given for the purpose of disclosure.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

(FIGS. 3A, 3B) Sagittal sections through the suprachiasmatic nucleus (SCN). (FIG. 3A) High expression levels of m-rigui2 in the suprachiasmatic nucleus at ZT12. (FIG. 3B) At ZT24, expression of m-rigui2 is no longer detected. (FIG. 3C) Expression of m-rigui2 in the hippocampus, piriform cortex (FIG. 3D) and the olfactory bulb (FIG. 3E) is constitutive. (FIG. 3F) Hybridization of sense m-rigui2 riboprobe in the olfactory bulb reveals a low background signal. Abbreviations: c, caudal, CA, cornu ammonis; d, dorsal, dg, dentate gyrus, gl, glomeruli, ml, mitral cell layer, p, periglomerular cells, pfc, piriform cortex, r, rostral, v, ventral. Scale bars correspond to 500 μm (FIGS. 3A, 3B, 3C and 3D), in (FIGS. 3E and 3F) scale bars correspond to 300 μm.

FIG. 9A shows a diagram which approximates a normalized phase response curve (PRC) for the CS7BL/6 mouse strain, modified from Schwartz and Zimmermann (1990). The PRC plots the amount of phase shift (i.e. clock resetting) as a function of the time of a light pulse applied at the circadian time indicated on the abscissa. Negative phase shifts are delays of the clock; positive phase shifts represent clock advances. The PRC consists of three regions: a non-responsive part which corresponds to the subjective day, a delay region where phase shifts are negative, and an advance region, representing positive phase shifts in response to light.

FIG. 9B shows the induction of mPer1 (m-Rigui1) and mPer2 (m-Rigui2) by a 15 min light pulse applied at the circadian times indicated. Endogenous mPer2 (m-rigui2) expression in control mice is low except for CT15, where residual expression is still detectable (top row). A light pulse induces this gene in a CT-dependent fashion (center row). Endogenous mPer1 (m-rigui1) expression is not seen at any of the CTs examined, but is induced by a light pulse in a CT-independent fashion (bottom row). Scale bar: 500 μm.

FIG. 9C shows a graphical representation of the relationship between mPer1 (m-rigui1) and mPer2 (m-rigui2) induction and phase delay evoked by a light pulse. The abscissa plots the phase shift taken from FIG. 9A, and the ordinate depicts the observed silver grain density seen in FIG. 9B. Open triangles and squares represent the mPer1 silver grain density in the right and left suprachiasmatic nucleus. Filled circles and squares represent the mPer2 (m-rigui2) silver grain density in the right and left suprachiasmatic nucleus.

In the case of mPer2 (m-rigui2), but not mPer1 (m-rigui1), the level of gene induction is correlated with the extent of phase shifting.

Figure 10:
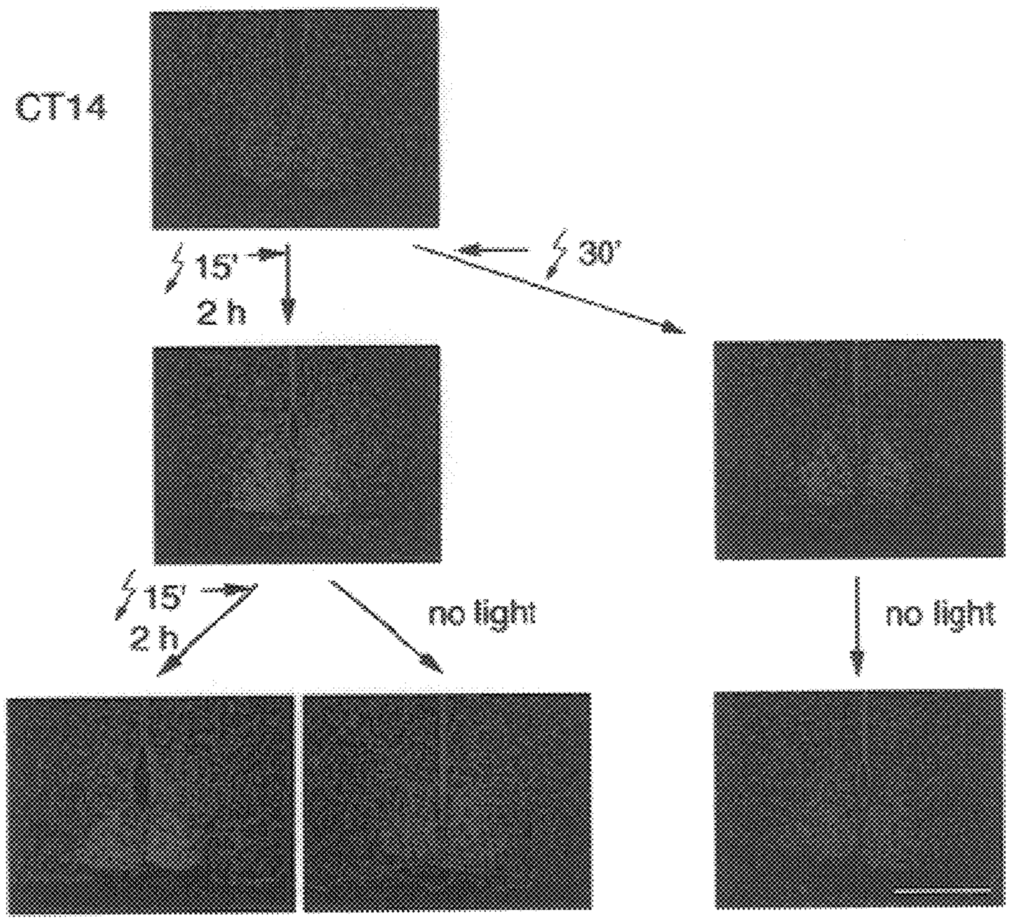

FIG. 10 shows the effect of a double light pulse at CT14 on mPer2 (m-rigui2) expression in the suprachiasmatic nucleus. mPer2 induction by a 15 or 30 min light pulse is strong. However, unless a second pulse is applied to reset the clock, expression reverts to background levels. Scale bar: 500 $\mu$m.

Figure 11:
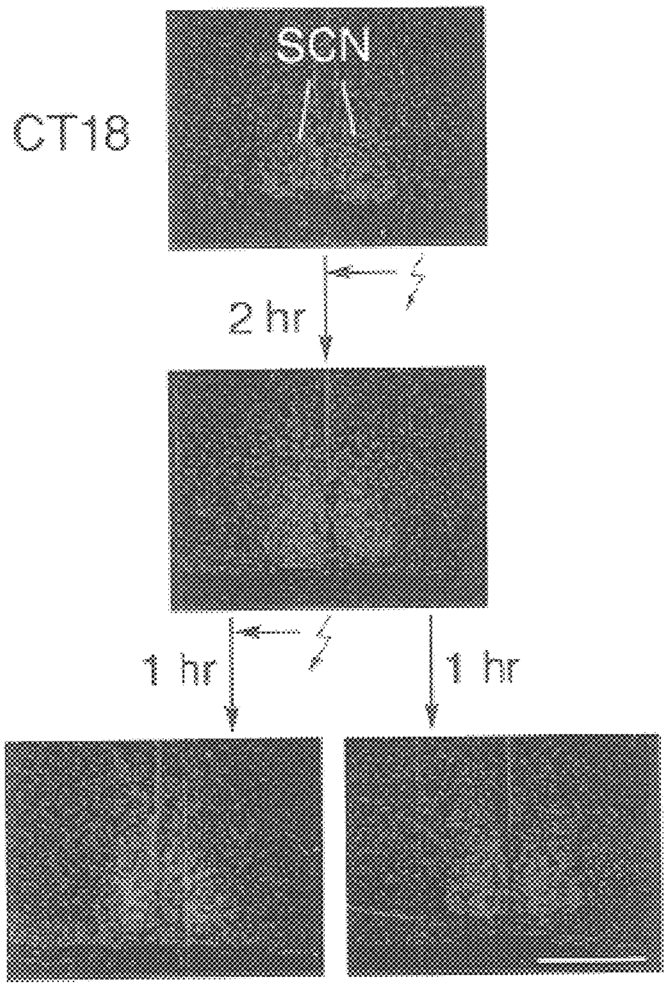

FIG. 11 shows the effect of a double light pulse at CT18 on mPer2 (m-rigui2) expression in the suprachiasmatic nucleus. A single 15 min light pulse applied at CT18 induced mPer2 weakly (see also FIG. 9B). However, as this treatment resets the clock backwards, a second 15 min pulse evokes strong mPer2 expression. The control suprachiasmatic nucleus that had not been exposed to a second pulse does not exhibit mPer2 expression. Scale bar: 500 $\mu$m.

DETAILED DESCRIPTION OF THE INVENTION

A RIGUI-like human gene, KIAA0347 (KIAA is an acronym used by Kazusa DNA Research Institute to name their cDNA clones), was noted in the Genbank data base (Sun et al., 1997). The present invention demonstrates the isolation of the mouse homolog of the RIGUI-like human gene and demonstrates high sequence homology with the m-rigui1 protein. Therefore, the gene of the present invention is termed m-rigui2. To show whether m-rigui2 behaved as a circadian clock component, mice were subjected to various light-dark cycle conditions, and their brains were analyzed for m-rigui2 gene expression. Such experiments revealed diurnal expression of m-rigui2 in the suprachiasmatic nucleus, the ability of this gene to be expressed in a free-running manner, and its ability to be synchronized by an external light cue. Similar findings were reported for m-rigui1 (Sun et al., 1997; Tei et al., 1997), but the zeniths of expression of m-rigui1 and m-rigui2 differ by approximately 4 hours. The striking response of these genes to environmental light in an entrainment experiment raises the possibility that expression of the m-rigui genes is light-inducible, as had been reported for frequency, the pacemaker gene of *Neurospora crassa* (Crosthwaite et al., 1995). In the retinorecipient region of the suprachiasmatic nucleus, m-rigui1 but not m-rigui2 is rapidly induced by a pulse of light at CT22. Thus, m-rigui1 may not only be a clock component but also a target of the light-activated input pathway of the circadian machinery.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomeclature, *J Biol. Chem.,* 243:3552–59 (1969), abbreviations for amino acid residues are as is known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the -10 and -35 consensus sequences.

A "nucleotide polymorphism" refers to changes in nucleotides(s) that does not affect the encoded amino acids or if it leads to a change in an encoded amino, it has a neutral effect.

An "exon" is an expressed sequence transcribed from the gene locus.

An "intron" is a non-expressed sequence that is from the gene locus.

A "cis-element" is a nucleotide sequence that encompasses the gene locus that interacts with other proteins which can upregulate or downregulate expression of a specicif gene locus.

A "gene locus" is a region of the genome that encodes for a specific gene. The term "gene locus" includes the promoter, cis-elements, and exon and intron sequences that embody the messenger RNA.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

A "homodimer" refers to the expressed protein product dimerized to form a functional molecule.

A "heterodimer" refers to an expressed protein that forms a functional molecule with another protein.

A "protein bait" is a bait in a protein sequence that is encoded in part, or in whole by the gene locus which is used in an expression system like the "two-hybrid system" used in vivo to search the "protein-protein" interactions.

The term "induction of gene expression" refers to the induction of the gene by environmental cues, such as light, termperature, social/behavior activities and the use of hormones such as melatonin.

The regulation of daily RIGUI1 and RIGUI2 (also called PER1 and PER2) levels could be through phophorylation processes. Alternatively, regulation could be through specific protein proteases that degrade RIGUI1 and RIGUI2. These molecules are potential targets for drug development. Both RIGUI1 and RIGUI2 have significant protein homology to known extracellular signal proteins that are involved in protein phosphorylation.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantitiy of both the label after which binding studies are conducted to determine the extent to which the labeled material binds to the cell receptors. In this way, differences in affinity between materials can be ascertained.

Another assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a human or mouse RIGUI proteins of the present invention can be used to transform a host using any of the techniques commonly known to those of ordinary skill in the art. Especially preferred is the use of a vector containing coding sequences for the gene which encodes a human or mouse RIGUI protein of the present invention for purposes of prokaryote transformation. Prokaryotic hosts may include *E. coli, S. tymphimurium, Serratia marcescens* and *Bacillus subtilis.* Eukaryotic hosts include yeasts such as *Pichia pastoris,* mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The invention includes a substantially pure DNA encoding a mouse m-rigui2 protein, a strand of which DNA will hybridize at high stringency to a probe containing a sequence of at least 15 consecutive nucleotides of SEQ ID No: 4. The protein encoded by the DNA of this invention may share at least 80% sequence identity (preferably 85%, more preferably 90%, and most preferably 95%) with the amino acids listed in SEQ ID No: 3.

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in SEQ ID No: 4) or the complement thereof. Such a probe is useful for detecting expression of RIGUI in a human cell by a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides (preferably 20, more preferably 30, even more preferably 50, and most preferably all) of the region from the nucleotides listed in SEQ ID NO: 4.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID No: 4) which encodes an alternative splice variant of RIGUI.

The DNA may have at least about 70% sequence identity to the coding sequence of the nucleotides listed in SEQ ID No: 4, preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The present invention comprises a vector comprising a DNA sequence which encodes a m-rigui2 protein and said vector is capable of replication in a host which comprises, in operable linkage: a) an origin of replication; b) a promoter; and c) a DNA sequence coding for said protein. Preferably, the vector of the present invention contains a portion of the DNA sequence shown in SEQ ID No: 4. A "vector" may be defined as a replicable nucleic acid construct, e.g., a plasmid or viral nucleic acid. Vectors may be used to amplify and/or express nucleic acid encoding a m-rigui2 protein. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure m-rigui2 protein may be obtained, for example, by extraction from a natural source; by expression of a recombinant nucleic acid encoding an m-rigui2 polypeptide; or by chemically synthesizing the protein. Purity can be measured by any appropriate method, e.g., column chromatography such as immunoaffinity chromatography using an antibody specific for m-rigui2, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the m-rigui2 protein. As used herein, "fragment," as applied to a polypeptide, will ordinarily be at least 10 residues, more typically at least 20 residues, and preferably at least 30 (e.g., 50) residues in length, but less than the entire, intact sequence. Peptide fragments generated by recombinant methods range up to about several hundred residues but less than the intact protein sequence. Fragments of the m-rigui2 protein can be generated by methods known to those skilled in the art, e.g., by enzymatic digestion of naturally occurring or recombinant m-rigui2 protein, by recombinant DNA techniques using an expression vector that encodes a defined fragment of m-rigui2, or by chemical synthesis. The ability of a candidate fragment to exhibit a characteristic of m-rigui2 (e.g., binding to an antibody specific for m-rigui2) can be assessed by methods described herein. Purified m-rigui2 or antigenic fragments of m-rigui2 can be used to generate new antibodies or to test existing antibodies (e.g., as positive controls in a diagnostic assay) by employing standard protocols known to those skilled in the art. Included in this invention are polyclonal antisera generated by using m-rigui2 or a fragment of m-rigui2 as the immunogen in, e.g., rabbits. Standard protocols for monoclonal and polyclonal antibody production known to those skilled in this art are employed. The monoclonal antibodies generated by this procedure can be screened for the ability to identify recombinant m-rigui2 cDNA clones, and to distinguish them from known cDNA clones. Poly antisera can also be generated by direct injection of m-rigui1 or m-rigui2 cDNA under an expression cassette into animals. Naked DNA injection has been demonstrated to be an effective method to produce peptide in muscle cells.

Further included in this invention are m-rigui2 proteins which are encoded at least in part by portions of SEQ ID NO. SEQ ID No: 3, e.g., products of alternative mRNA splicing or alternative protein processing events, or in which a section of m-rigui2 sequence has been deleted. The fragment, or the intact m-rigui2 polypeptide, may be covalently linked to another polypeptide, e.g. which acts as a label, a ligand or a means to increase antigenicity.

The invention also includes a polyclonal or monoclonal antibody which specifically binds to m-rigui2. The invention encompasses not only an intact monoclonal antibody, but also an immunologically-active antibody fragment, e.g., a Fab or $(Fab)_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g. a radioactive label, non-radioactive isotopic label, fluorescent label, chemiluminescent label, paramagnetic label, enzyme label, or calorimetric label. Examples of suitable toxins include diphtheria toxin, Pseudomonas exotoxin A, ricin, and cholera toxin. Examples of suitable enzyme labels include malate hydrogenase, staphylococcal nuclease, delta- 5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^{3}H$, $^{125}I$, $^{131}I$, $^{32}P$, $^{35}S$, $^{14}C$, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472–480; Shreve et al., (1986) *Magn. Reson. Med.* 3, 336–340; Wolf, G. L., (1984) *Physiol. Chem. Phys. Med. NMR* 16, 93–95; Wesbey et al., (1984) *Physiol. Chem. Phys. Med. NMR* 16, 145–155; Runge et al., (1984) *Invest. Radiol.* 19, 408–415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) *Clin. Chim. Acta* 70, 1–31; and Schurs et al., (1977) *Clin. Chim. Acta* 81, 1–40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

Also within the invention is a method of detecting m-rigui2 protein in a biological sample, which includes the steps of contacting the sample with the labelled antibody, e.g., radioactively tagged antibody specific for m-rigui2, and determining whether the antibody binds to a component of the sample.

A standard Northern blot assay can be used to ascertain the relative amounts of m-rigui2 mRNA in a cell or tissue obtained from a patient suspected of having cancer, in accordance with conventional Northern hybridization techniques known to those persons of ordinary skill in the art. This Northern assay uses a hybridization probe, e.g. radiolabelled m-rigui2 cDNA, either containing the full-length, single stranded DNA having a sequence complementary to SEQ ID No. 4, or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art.

The present invention is directed to DNA encoding a m-rigui2 protein selected from the group consisting of: (a) isolated DNA which encodes a m-rigui2 protein; (b) isolated DNA which hybridizes to isolated DNA of (a) above and which encodes a m-rigui2 protein; and (c) isolated DNA differing from the isolated DNAs of (a) and (b) above in codon sequence due to the degeneracy of the genetic code, and which encodes a m-rigui2 protein. Preferably, the DNA has the sequence shown in SEQ ID No. 4. More preferably, the DNA encodes a m-rigui2 protein having the amino acid sequence shown in SEQ ID No. 3.

The present invention is also directed to a vector capable of expressing the DNA of the present invention adapted for expression in a recombinant cell and regulatory elements necessary for expression of the DNA in the cell. Preferably, the vector contains DNA encoding a m-rigui2 protein having the amino acid sequence shown in SEQ ID No. 3.

The present invention is also directed to a host cell transfected with the vector described herein, said vector expressing a m-rigui2 protein. Representative host cells include consisting of bacterial cells, mammalian cells and insect cells.

The present invention is also directed to a isolated and purified m-rigui2 protein coded for by DNA selected from the group consisting of: (a) isolated DNA which encodes a m-rigui2 protein; (b) isolated DNA which hybridizes to isolated DNA of (a) above and which encodes a m-rigui2 protein; and (c) isolated DNA differing from the isolated DNAs of (a) and (b) above in codon sequence due to the degeneracy of the genetic code, and which encodes a m-rigui2 protein. Preferably, the isolated and purified m-rigui2 protein has the amino acid sequence shown in SEQ ID No. 3.

The present invention is also directed to a method of detecting expression of the m-rigui2 protein, comprising the steps of: (a) contacting mRNA obtained from the cell with the labeled hybridization probe; and (b) detecting hybridization of the probe with the mRNA. Preferably, the probe consists of a portion of the DNA of SEQ ID No. 4.

The following examples are given for the purpose of illustrating various embodiments of the invention and are not meant to limit the present invention in any fashion.

EXAMPLE 1

RT-PCR and Screening of cDNA Libraries

A PCR fragment for m-rigui2 was obtained by using primers derived from the KIAA 0347 sequence in the GenBank data base (Accession No: AB002345). Primers used were:

5'-GCAGGAAGATGTGGACATGAGC-3' (SEQ ID No 1)

5'-GGTCAGAGATGTACACCATCTTCC-3' (SEQ ID No 2)

First strand cDNA was generated by oligo dT-priming of 1 $\mu$g of mouse brain mRNA in a 20 $\mu$l reaction using Moloney reverse transcriptase (BRL-GIBCO). The PCR reactions were carried out in 50 $\mu$l containing 0.5 Units of Taq/pfu polymerase (20:1), 125 $\mu$M of dNTP, 1 $\mu$M of primers and PCR extend buffer (purchased from Stratagene). One $\mu$l of the first strand cDNA synthesis reaction mixture was added as a template to the amplification reaction mixture. Following denaturation at 95° C. for 3 minutes, the 30 cycles of amplification were performed under the following conditions: 30 seconds at 94° C., 30 seconds at 50° C. and 3 minutes at 70° C. The PCR products were visualized on a 1% agarose gel. The PCR product was gel purified and subcloned into pCR vector (Stratagene). The cloned PCR product was sequenced and identified as the mouse homolog of KIAA 0347. The mouse full-length cDNA was obtained by screening a mouse brain cDNA library (BRL-GIBCO) (Sambrook et al., 1989). The nucleotide sequence of both strands of the m-rigui2 cDNA was determined using DNA sequencing reaction kits and an ABI 373A instrument and is shown in TABLE 1.

TABLE I

| Full Length cDNA Sequence of m-rigui2 |
|---|
| 1 CGGGAGGGCG ACGCGGCGGC AGCGGCGCTA CTGGGACTAG CGGCTCCGGG |
| 51 CGGCTGCGGC GCAGGCCGAG CGCACCAAGT GACGGGCCGA GCAAGGGACA |
| 101 GACGCGCGGG TTGACGCGGC GAAGCGCTTA TTCCAGAGCC CGACATGAAT |
| 151 GGATACGTGG ACTTCTCCCC AAGTCCCACC AGTCCCACCA AGGAGCCAGG |
| 201 GGCACCTCAG CCCACCCAGG CTGTGCTCCA GGAAGACGTG GACATGAGCA |
| 251 GTGGCTCCAG CGGAAACGAG AACTGCTCCA CGGGACGGGA CTCTCAGGGC |
| 301 AGTGACTGCG ACGACAATGG GAAGGAGCTG CGGATGCTCG TGGAATCTTC |
| 351 CAACACTCAC CCCAGCCCTG ATGATGCCTT CAGACTCATG ATGACAGAGG |
| 401 CAGAGCACAA CCCCTCCACG AGCGGCTGCA GTAGTGAGCA GTCTGCCAAA |
| 451 GCTGACGCAC ACAAAGAACT GATAAGGACC CTGAAGGAGC TGAAGGTCCA |
| 501 CCTCCCTGCA GACAAGAAGG CCAAGGGGAA GGCCAGCACG CTGGCAACCC |
| 551 TGAAGTATGC CCTGCGGAGC GTGAAGCAGG TGAAGGCTAA TGAGGAGTAC |
| 601 TACCAGCTGC TAATGTCCAG TGAGAGCCAG CCCTGCAGTG TGGATGTGCC |
| 651 TTCCTACAGC ATGGAGCAGG TTGAGGGCAT TACCTCCGAG TATATCGTGA |
| 701 AGAACGCGGA TATGTTTGCT GTGGCTGTGT CCCTGGTTTC TGGGAAGATC |
| 751 CTGTACATCT CTAACCAAGT GGCCTCCATC TTTCACTGTA AGAAGGACGC |
| 801 CTTCAGTGAT GCCAAGTTTG TGGAGTTCCT GGCTCCTCAT GACGTCAGTG |
| 851 TGTTCCACAG CTACACCACC CCTTACAAGC TTCCGCCCTG GAGTGTGTGC |
| 901 AGCGGCTTAG ATTCTTTCAC TCAGGAGTGC ATGGAGGAGA AATCTTTTTT |
| 951 CTGCCGTGTC AGTGTTGGGA AACACCACGA GAATGAGATT CGCTACCAGC |
| 1001 CCTTCCGCAT GACACCCTAC CTGGTCAAGG TGCAAGAGCA GCAGGGTGCT |
| 1051 GAGAGCCAGC TCTGCTGCCT GCTGCTGGCA GAGAGGGTAC ACTCGGGCTA |
| 1101 TGAAGCGCCT AGAATCCCTC CTGAGAAGAG GATCTTCACA ACAACCCACA |
| 1151 CACCAAACTG CTTGTTCCAG GCTGTGGATG AAAGGGCGGT CCCCCTCCTG |
| 1201 GGCTATCTAC CTCAGGATCT GATCGAGACG CCTGTGCTCG TGCAGCTCCA |
| 1251 CCCCAGCGAC CGGCCCTTGA TGCTCGCCAT CCACAAGAAG ATCCTACAGG |
| 1301 CCGGTGGACA GCCTTTCGAT TATTCTCCCA TTCGATTCCG CACCCGCAAC |
| 1351 GGGGAGTACA TCACACTGGA CACTAGCTGG TCCAGCTTCA TCAACCCGTG |
| 1401 GAGCAGGAAG ATATCTTTCA TCATTGGGAG GCACAAAGTC AGGGTAGGCC |
| 1451 CTTTGAATGA GGATGTGTTC GCAGCTCCCC CGTGCCCAGA GGAGAAGACT |
| 1501 CCGCACCCCA GCGTTCAGGA GCTCACAGAA CAAATCCACC GGCTACTGAT |
| 1551 GCAGCCTGTC CCCCACAGCG GCTCCAGTGG CTATGGGAGC CTGGGCAGTA |
| 1601 ACGGATCCCA CGAACACCTC ATGAGCCAGA CATCATCCAG CGACAGCAAT |
| 1651 GGCCAAGAGG AGTCTCACCG GAGGAGATCC GGAATTTTTA AAACCAGTGG |
| 1701 CAAGATTCAA ACCAAAAGTC ACGTTTCTCA TGAGTCTGGA GGACAGAAGG |
| 1751 AAGCATCTGT TGCAGAAATG CAAAGCAGCC CCCCAGCTCA GGTGAAAGCT |
| 1801 GTCACCACCA TAGAAAGGGA CAGCTCAGGG GCCAGCCTAC CCAAGGCCAG |
| 1851 CTTCCCAGAG GAACTAGCCT ATAAGAACCA GCCTCCTTGC TCCTACCAGC |
| 1901 AGATCAGCTG CCTGGACAGT GTCATCAGGT ACCTGGAGAG CTGCAGCGAG |

TABLE I-continued

| Full Length cDNA Sequence of m-rigui2 |
|---|
| 1951 GCAGCCACCC TGAAAAGGAA GTGCGAGTTC CCAGCCAACA TCCCATCCCG |
| 2001 GAAGGCCACA GTCAGCCCCG GGCTGCACTC TGGAGAGGCA GCGCGGCCCT |
| 2051 CCAAGGTGAC CAGCCACACA GAGGTCAGTG CTCACCTGAG CTCCCTGACG |
| 2101 CTGCCAGGCA AGGCCGAGAG TGTGGTGTCC CTCACCAGCC AGTGCAGCTA |
| 2151 CAGCAGCACC ATCGTGCATG TGGGCGACAA AAAGCCACAG CCCGAGCTAG |
| 2201 AGACGGTAGA AGATATGGCC AGTGGGCCCG AGTCCCTGGA TGGTGCGGCC |
| 2251 GGCGGCCTCA GCCAAGAAAA GGGGCCTCTT CAGAAGTTGG GCCTCACCAA |
| 2301 GGAAGTTCTG GCTGCACATA CACAGAAAGA GGAGCAGGGC TTCCTGCAGA |
| 2351 GGTTCAGGGA GGTGAGCAGG CTCAGTGCCC TGCAGGCTCA CTGCCAGAAC |
| 2401 TATCTCCAGG AGCGGTCCCG AGCCCAGGCG AGTGATCGAG GACTAAGAAA |
| 2451 TACTTCTGGA CTAGAGTCAT CTTGGAAAAA AACTGGAAAG AACAGGAAAC |
| 2501 TGAAGTCAAA ACGCGTCAAG ACTCGGGACT CTTCTGAGAG CACAGGGTCT |
| 2551 GGAGGACCAG TGTCCCACCG ACCTCCCCTC ATGGGCCTGA ATGCCACAGC |
| 2601 CTGGTCACCC TCCGACACAT CCCAGTCCAG CTGCCCCTCT GCACCCTTCC |
| 2651 CCACCGCAGT GCCAGCTTAC CCCCTACCTG TGTTCCAGGC ACCCGGAATA |
| 2701 GTATCCACAC CAGGGACGGT GGTGGCGCCA CCTGCAGCCA CCCACACTGG |
| 2751 CTTCACCATG CCTGTTGTGC CTATGGGCAC CCAGCCTGAA TTCGCAGTGC |
| 2801 AGCCCCTGCC ATTCGCTGCC CCTTTGGCTC CTGTCATGGC CTTCATGCTG |
| 2851 CCCAGCTACC CGTTCCCACC AGCAACCCCA AACCTGCCTC AGGCCTTCCT |
| 2901 CCCCAGCCAG CCTCACTTTC CAGCCCACCC CACACTTGCC TCCGAAATAA |
| 2951 CTCCTGCCTC CCAGGCTGAG TTCCCTAGTC GGACCTCGAC GCTCAGACAG |
| 3001 CCGTGCGCTT GCCCAGTCAC CCCTCCAGCC GGCACAGTGG CCCTGGGCAG |
| 3051 AGCCTCCCCA CCGCTCTTCC AGTCCAGAGG CAGTAGTCCC CTACAACTTA |
| 3101 ACCTGCTTCA GCTAGAGGAG GCGCCTGAAG GCAGCACTGG AGCCGCAGGG |
| 3151 ACCCTGGGGA CCACAGGGAC AGCAGCTTCT GGTCTGGACT GCACATCTGG |
| 3201 CACATCTCGG GATCGGCAGC CAAAGGCACC TCCAACATGC AACGAGCCCT |
| 3251 CAGACACTCA GAACAGTGAT GCCATCTCCA CGTCAAGTGA CCTGCTCAAC |
| 3301 CTCCTTCTGG GCGAGGACCT CTGCTCGGCC ACTGGCTCAG CCCTGTCTAG |
| 3351 AAGCGGGGCA TCCGCCACCT CAGACTCTCT GGGCTCCAGC TCGCTGGGCT |
| 3401 TCGGCACATC CCAAAGTGGG GCAGGCAGTA GTGACACAAG TCACACCAGC |
| 3451 AAATACTTTG GAAGCATTGA CTCTTCAGAG AATAATCACA AAGCAAAAAT |
| 3501 GATCCCAGAC ACGGAGGAAA GCGAGCAGTT CATTAAGTAC GTCTTGCAGG |
| 3551 ACCCCATCTG GCTGCTGATG GCCAACACAG ACGACAGCAT CATGATGACA |
| 3601 TACCAGCTGC CCTCCCGGGA TCTCCAGGCG GTGTTGAAGG AGGACCAGGA |
| 3651 GAAGCTGAAG CTGCTGCAGA GGTCCCAGCC CCGGTTCACA GAGGGCCAGA |
| 3701 GGCGAGAGCT CCGAGAGGTT CATCCGTGGG TCCACACTGG GGGCCTGCCT |
| 3751 ACGGCCATCG ATGTGACAGG CTGTGTTTAC TGCGAGAGTG AGGAGAAAGG |
| 3801 CAACATTTGC CTGCCATATG AGGAAGACAG TCCTTCCCCG GGACTCTGTG |

TABLE I-continued

| Full Length cDNA Sequence of m-rigui2 |
| --- |
| 3851 ATACCTCAGA AGCCAAAGAG GAGGAAGGTG AACAGCTGAC AGGCCCCAGG |
| 3901 ATAGAGGCCC AGACGTAACC CTGTCCCCCA GCCAGAGGTC GACATTAGAC |
| 3951 GGTGCTCGGA AGAAGGGGGA AGATCTTGTG GTTTCTAATC ACATGGACCC |
| 4001 ATACCTACAC TGCTTTTTTT GTTTTAGGAA AAACAAAAAA CAAAAACACC |
| 4051 ATAGTTTTCT GGCGGTGGAA CAAAACTGAG GGGAGGTTTA GGAGGAAATC |
| 4101 CATTTTTGTA TTAAAATAGA AATACGGAAT TTGGGGGATG GGGTGAGATT |
| 4151 CGTCATTGAA CTTGAGACTG AGGTGGTCTG TGTTGTCATG GAGGCTGCCT |
| 4201 CATGGTCCTC AGGAGTGTCT TGACCTCCAT GAAACCTCTT TCCAGTGTGC |
| 4251 CAATGTCCTC TGGCCCCTGT GGATTGTTCT GAAACATAAC ACCAGGATGT |
| 4301 GGCAGGTAAC AGGGAAGCCA CAAGAGGCTA TCCACCAAGG GCCCAGCTTT |
| 4351 CTGGAACTTT CTCACAGTGT GATTGTATCT CCCAAGCAGA GAGACCATCT |
| 4401 CTCCTGACAT CCTCTCAGTG TGTTCCCTTA CGTGGTTTGG AGCATGGTGT |
| 4451 AGCAGCTTTG GCTTCAGGTC CTGCCTGTGG TGGTCAACAT TCCAGTCTGA |
| 4501 CATGGCTTCT GTTCGTCAAC AAAGTTGAAA TGCCTGCTCT GGACTAGTGG |
| 4551 AGCTCAGTGG CTTCTGCAAA CGATGCCCAC CATCAGACTA GCACCCCCAC |
| 4601 ACTGTACATT TCTCTGCTGT TCTTGTATCC TTTTTAGACC ATTGTGGCCA |
| 4651 GTGTGCAGAG AGAGCTGTGG CATCATCAGC CATGTTGCCG TGTCTGCATG |
| 4701 GTGGCCTCTG CAAGCCAGGC TTTGTTGCTG TAGAGGACAC CGTCACGTGT |
| 4751 TTGTTCTTTG GTTGGACTCT CTCAGACATT AGCTCCCAGC AGAAAGCAGC |
| 4801 CACTGAGCAC GGAGGAGAGA GGCACCCACA CTGCTGCCCT GAGTTCTCCA |
| 4851 GTTTGCAGGG AGCTCAGCCT CCCACTCTAT ATGTATATAC TCCTAGCTAC |
| 4901 TGTGGCTTCG GGTCTCTGTC ACATCTATCT GTGCTGCTGG TCCTCAGATC |
| 4951 ACTGGAACCT GTGGAGAGAA GGGGACCTCT CTGCCCAGCT CTACAAAACT |
| 5001 TTATGCTGCA TCAGACATCC AAAGATTGTT CCGACATGCT TGCGGGTGAC |
| 5051 CCCTGGTGGA ACGAGACATC ACCAGTGAGG AATCATTGGA CTTAAAAGTA |
| 5101 GACAAAGCCT GGAGCAGAGG AAGCTGTTTC CTGAGTCTGA AGTGGCTACT |
| 5151 GGGGACATGT CCTGCTGTAG TTGGTTTTCA TGGTAAAGCC ATCTGAGGCC |
| 5201 TGAATATTAC CCCTATTTTT CATAAACACA AGAACTCTAT TTTTTTTATT |
| 5251 AAAGCAACAC CACCTTTCAC AGTGATCAGG TAGTAGCCAT GTTTTAAAGG |
| 5301 AAATTCAATG TTACAGACAG CTGCCTCTCT GACCAGTCTG ATCCTAAGGG |
| 5351 TAGATAGAAG ATGGTCTAAG CCTACGCTTG TTACTTAAAC ACAAAACTGC |
| 5401 CAAAACCTTC TCTCTTCTCT CTTGAATGTT TACCATCAGC GTTATTTTAT |
| 5451 GATTATTTAA TATATAGTCC TTGATTGTTA ACTGCTAAGA AGTTGACTTC |
| 5501 CTAdGATAAT TTTGTGAATC TGTTTACAAG ATGCCAAGCA TCCAGCCCTG |
| 5551 TTTTCTTTAG AATGTGTGCT TACACGGGTG TCCTAAGACA TTCTCTATTT |
| 5601 TAAACTGAGC CTTCTTTTTA ATGTAAATAA GCTCTCAGAG TTTGTGCGAT |
| 5651 GATGATTCGT GAGCCTTGCC GGACAAGAGG TTTGTTCATG CGCAAACCAA |
| 5701 ACGTACCTTC ACCCAGTGCA ATATATTTGT GTGACTGCTT GTGTCTTTTT |

TABLE I-continued

| Full Length cDNA Sequence of m-rigui2 |
|---|
| 5751 ATGACTTTTT TGCCTTTTAG AAAATTGTTA AATAAAGCAA GTATATTTTT |
| 5801 ATTTTCAAAA AAAAAA |

EXAMPLE 2

Specimen Preparation and Histology

The 129SvEvBrd and C57BL/6J mouse strains were provided by Dr. Allan Bradley. All animals were kept in separate cages under the condition of 12 hour light and 12 hour dark cycle for at least two weeks prior to their use in the respective experiments. For free-running condition, the mice were maintained in a room with lights completely turned off. The 12 hour light/12 hour dark cycle and entrainment experiments were carried out. For the light induction experiments animals were exposed to a 15 minute light pulse at CT22 using fluorescent lightbulbs providing 550 foot-candles (50 lux) in the cage of the mice. Animals were then returned to the dark environment and brains were dissected at various times. Control mice not exposed to light were collected at CT22 and CT24. Mice were sacrificed by cervical dislocation and the brain was removed and fixed in ice-cold 4% paraformaldehyde for 16 to 20 hours. Tissue was dehydrated and embedded in paraffin and sectioned at a thickness of 7 $\mu$m. Animals collected under dark conditions were dissected under a 15 W safety red light.

EXAMPLE 3

RNA in situ Hybridization

In situ hybridization was carried out as described (Albrecht et al., 1997a, 1998). Antisense and sense riboprobes were synthesized with T3 or T7 RNA polymerase in the presence of a $^{35}$S-UTP (1,250 Ci/mmol, Du Pont NEN, Charlotte, N.C.). The m-rigui1 probe was made from a cDNA corresponding to nucleotides 620 to 1164 (Accession number: AF022992). The m-rigui2 probe was made from a cDNA corresponding to nucleotides 229 to 768 (bankit 157815). The c-fos probe was made from a mouse cDNA whose nucleotide sequence corresponds to amino acid positions 237 to 332. Hybridization was done overnight at 55° C. Stringency washes were performed at 64° C. (m-rigui1 and m-rigui2) and 63° C. (c-fos). Slides were dipped in NTB-2 emulsion and exposed for 3 to 6 days. Tissue was visualized by fluorescence of Hoechst dye-stained nuclei (blue color in figures). Silver grains (yellow=m-rigui1, red=m-rigui2, white=c-fos) were visualized by dark-field illumination. Images are videographs captured in Adobe Photoshop.

EXAMPLE 4

Isolation and Characterization of m-rigui2 cDNAs

Since the expression of m-rigui1 displays expression properties expected from a circadian gene, whether other genes that encode proteins homologous to m-rigui1 have a similar function was examined. The protein sequence encoded by the human RIGUI gene was used to search the Genbank data base. BLAST and FASTA searches revealed high sequence similarity of the open reading frame (ORF) of RIGUI1 with an ORF encoded by a human cDNA designated as KIAA0347 (Nagase et al., 1997). A BLAST search yielded a homology probability score P(N) of 7.1 $e^{-271}$ between RIGUI1 and KIAA0347. As a point of reference, the score between RIGUI and the Drosophila period gene product was 2.2 $e^{-23}$. RIGUI and KIAA0347 are 47% identical and 70% homologous (identity, conserved and neutral substitutions).

Figure 1:
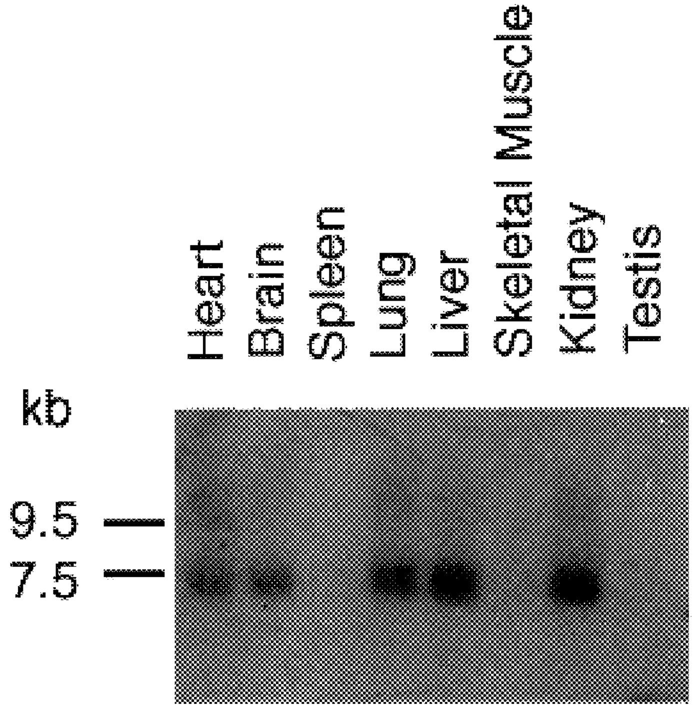
FIG. 1 shows the northern blot of adult mouse tissues probed with m-rigui2. A predominant band of about 7 kb was detected. This only indicates the major transcript size although alternative splice forms of this gene can still be present and was undetected by this method.

To identify the mouse homolog of this human gene, a RT-PCR technique using mouse brain cDNA as the template was applied. The nucleotide sequence of the isolated 539 nucleotide long PCR product was 81% identical to KIAA0347, suggesting that the mouse homolog of this gene had been isolated. A Northern blot was probed with the PCR fragment and revealed a predominant band at about 7 kb in most mouse tissues (FIG. 1). m-rigui1 was expressed in the same tissues and also in skeletal muscle and in testis (Sun et al., 1997).

Figures 1, 2:
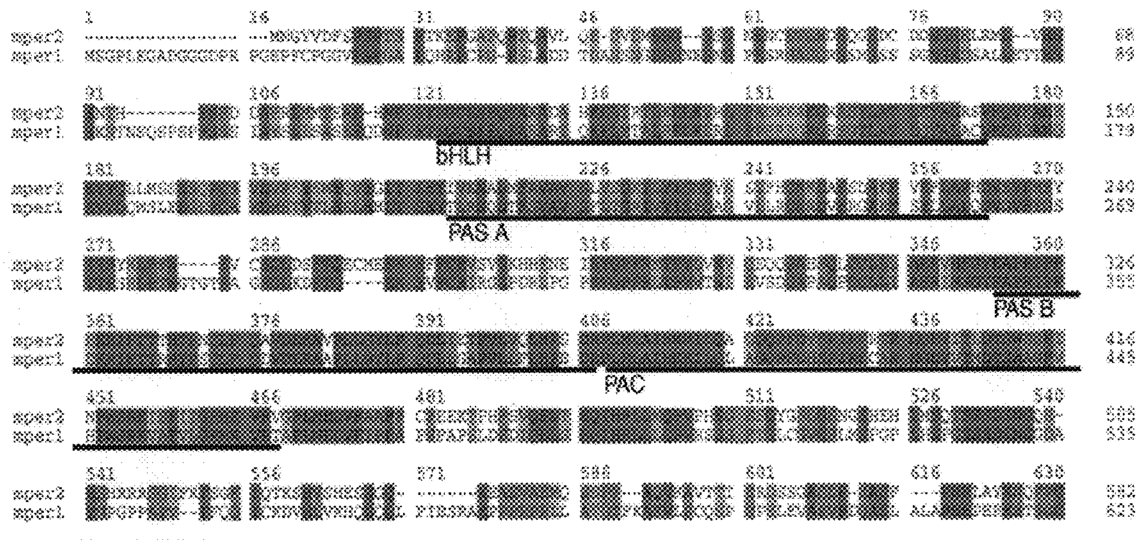
FIG. 2 shows the comparison of the predicted protein sequences of m-rigui1 (SEQ ID No: 5) and m-rigui2 (SEQ ID NO 3). Alignment of the two protein sequences was carried out by the pattern-induced multi-sequence alignment program (PIMA) and revealed marked identity between them (Smith and Smith, 1992). The amino acids shaded in red are identical, those shaded in blue are conserved substitutions and those shaded in green are neutral substitutions. The bHLH motif, the PAS A, PAS B and the PAC motifs are indicated by horizontal lines. The PAS A, PAS B and PAC motifs constitute the PAS domain.
Figure 2:
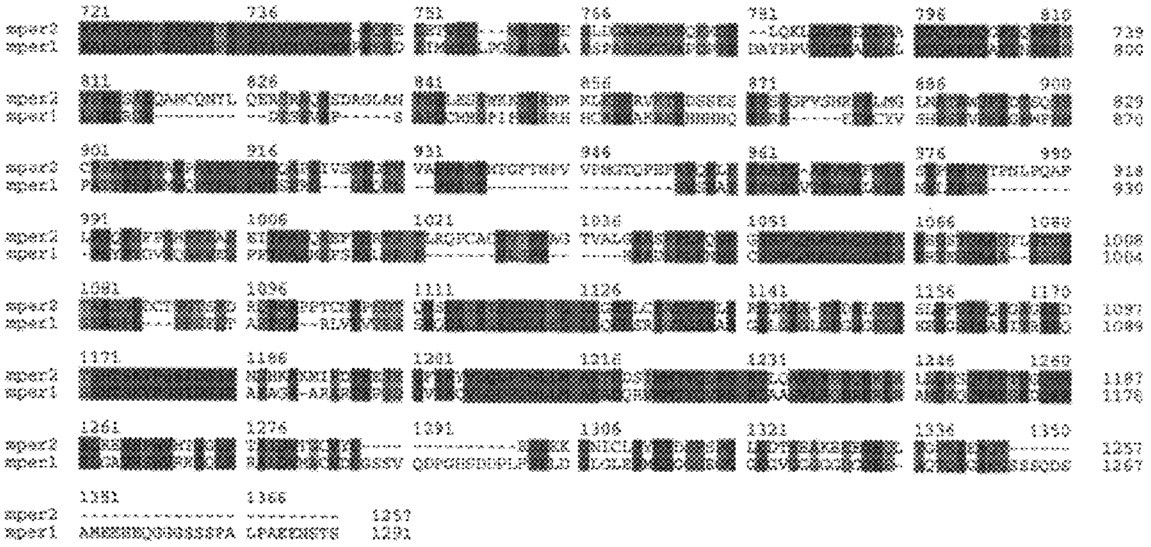

To obtain a longer cDNA, an adult mouse brain cDNA library were screened with the 539 nucleotide PCR probe and seven cDNAs was identified. Restriction enzyme mapping suggested that these clones were overlapping fragments of the same gene. A cDNA of about 6 kb in length was sequenced in both directions, and translated into an open reading frame consisting of 1257 amino acids (SEQ ID No: 3) (FIG. 2). Protein sequence comparison between m-rigui1 and the mouse gene of the present invention revealed 47% identity. When including conserved and neutral substitutions, homology was 70% (FIG. 2). In the PAS domain the amino acid sequence identity was 61%. This domain is involved in protein-protein interactions (Huang et al., 1993; Lindebro et al., 1995; Zelzer et al., 1997) and was initially observed in *D. melanogaster* period (Per), in human aryl hydrocarbon receptor nuclear translocator protein (ARNT) and the Drosophila single minded protein (SIM). The PAS domain encompasses approximately 260 amino acids and contains two imperfect repeats of about 50 amino acids each (PAS A and PAS B motifs, FIG. 2). In addition, there is a 40–45 amino acid region C-terminal to the PAS B repeat, known as the PAC motif (Ponting and Aravind, 1997). As shown below, the mouse gene of the present invention displays a circadian rhythm of expression. This feature, and the sequence homology to m-rigui1 (FIG. 2), suggests that a member of the rigui family of PAS domain proteins was isolated. Accordingly, this gene was named m-rigui2.

Use of the PHDsec program (EMBL) for secondary structure analysis, revealed that the N-terminal region of m-rigui1 contains a putative basic helix-loop-helix (bHLH) motif (Sun et al., 1997). The m-rigui2 sequence was subjected to the same analysis. There are two helical regions, separated by about ten amino acids that may have conformations typical of a loop (FIG. 2). The m-rigui1 protein has three basic amino acid side chains in the putative basic region, whereas m-rigui2 has only two. Having such a bHLH motif would qualify the m-rigui proteins as transcription factors. However, given the low content of basic residues in the basic region, it remains uncertain whether riguis are indeed transcription factors. As a point of reference, known bHLH transcription factors have between 5 to 7 basic residues in the basic region, some of which make contact to the DNA (Ma et al., 1994).

Using BLAST and FASTA analysis, the sequence of m-rigui2 was compared to currently known PAS domain-containing proteins. Although there is significant homology between the PAS domains, the proteins are very divergent in the rest of the ORF, except for those listed in Table 2. This table compares the predicted sequences of the currently known PAS domain proteins implicated in circadian functions. The salient points of this comparison are: (1) m-rigui1 and m-rigui2 are the most homologous proteins; (2) m-rigui2 is closer to the Drosophila period gene product than m-rigui1. Specifically, the overall percent homology between m-rigui2 and Per is 53%, whereas this figure drops to 44% when comparing m-rigui1and Per. This is the main reason for not referring to m-rigui1 as m-per (see Tei et al., 1997); (3) The clock protein, the only mammalian PAS domain protein for which there is functional evidence for involvement in circadian rhythms (King et al., 1997), is distantly related to the period/rigui family members. Since m-rigui2 is related to m-rigui1, it is possible that m-rigui2 is also part of the circadian oscillator.

TABLE 2

| Compared sequences | P(N) entire ORF | P(N) PAS domain |
|---|---|---|
| m-rigui1 / m-rigui2 | 7.1 $e^{-271}$ | 7.5 $e^{-132}$ |
| Dm Per / m-rigui1 | 2.2 $e^{-23}$ | 1.7 $e^{-24}$ |
| Dm Per / m-rigui2 | 3.0 $e^{-24}$ | 1.3 $e^{-24}$ |
| Dm Per / clock | 7.1 $e^{-9}$ | 5.0 $e^{-10}$ |
| m-rigui1 / clock | 1.6 $e^{-4}$ | 3.1 $e^{-6}$ |
| m-rigui2 / clock | 4.4 $e^{-4}$ | 6.6 $e^{-6}$ |

BLAST comparison between various circadian genes that contain a PAS domain. Dm per = *Drosophila melanogaster* period. P(N) is the probability of finding a segment pair with equal or greater match (Altschul et al., 1990)

EXAMPLE 5 m-rigui2 is Expressed in a Diurnal Pattern in the SCN

Putative circadian regulator molecules should have the following characteristics. First, their expression should oscillate with a 24 hour rhythm. Second, they should be expressed in the suprachiasmatic nucleus (SCN), a group of hypothalamic neurons functioning as master regulator of mammalian circadian rhythms (Ralph et al., 1990). Third, circadian expression must persist in the absence of environmental cues such as light (free running condition). Fourth, the intrinsic rhythm of expression should be reset by changes in the oscillation of environmental cues (entrainment). As shown below, m-rigui2 meets these criteria.

Figure 3:
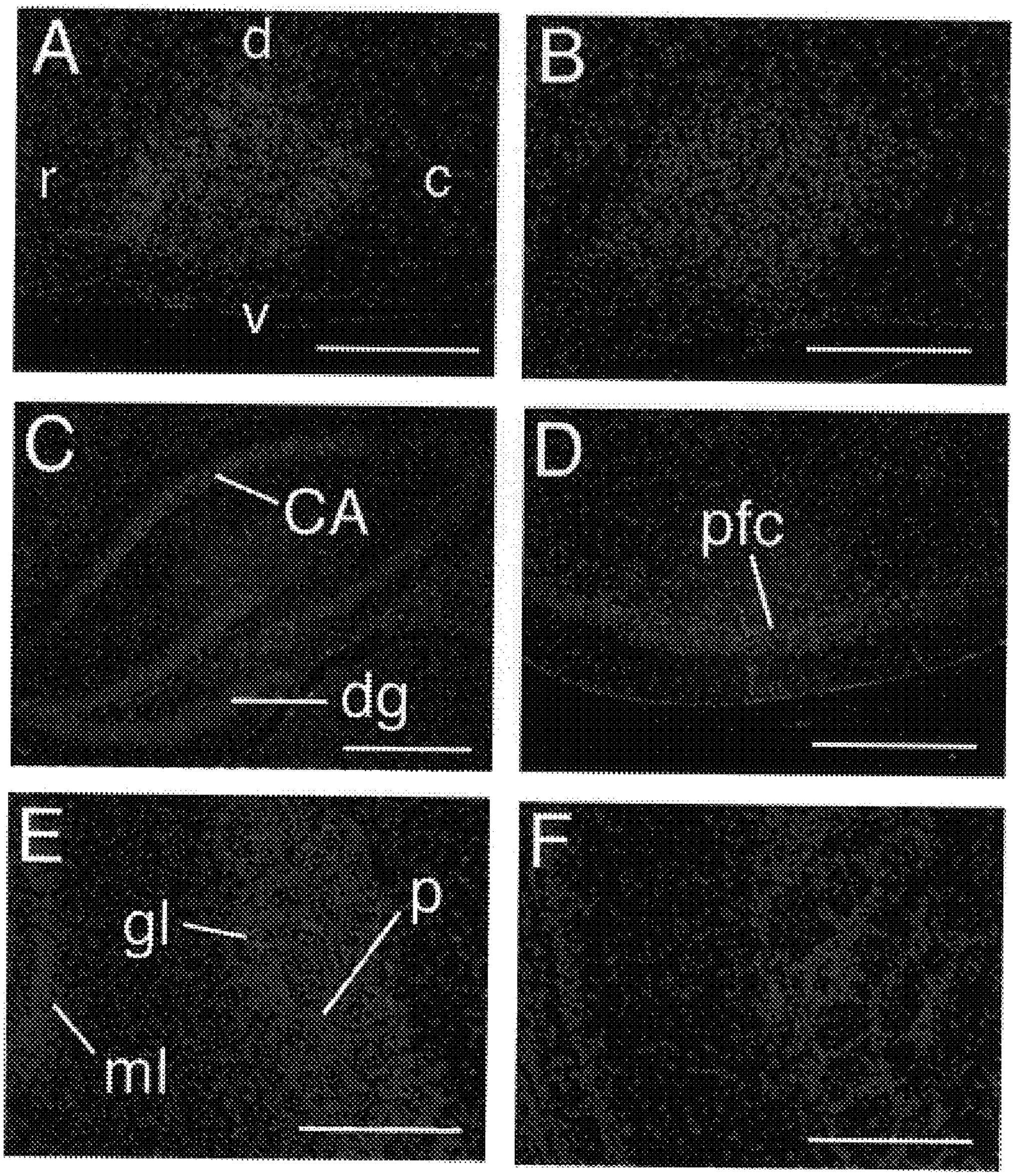
FIGS. 3A–3F show the expression of m-rigui2 in the mouse brain. All micrographs were taken from brains of 129/SvEvBrd male mice.

Expression of m-rigui2 in sections of brains from 129/SvEvBrd adult male mice were analyzed by in situ hybridization, using an antisense m-rigui2 riboprobe. Animals were kept in a 12 hour light/12 hour dark cycle, and were sacrificed at Zeitgeber Time (ZT) 12 and ZT24 (ZT0 is light on and ZT12 is light off). Expression of m-rigui2 was seen in the suprachiasmatic nucleus at ZT12 (FIG. 3A) but not at ZT24 (FIG. 3B). There was constitutive expression in the cornu ammonis and in the dentate gyrus of the hippocampus (FIG. 3C). Expression was also seen in the piriform cortex (FIG. 3D). In the olfactory bulb, transcripts are primarily found in the glomeruli, the region where the olfactory neurons form synapses with the mitral cells (FIG. 3E). Control hybridizations with m-rigui2 sense riboprobe show no significant signal (FIG. 3F). Expression in the cerebral cortex was low (data not shown). m-rigui2 expression in the pars tuberalis and the Purkinje neurons of the cerebellum was also examined. In 129/SvEvBrd mice, these tissues expressed m-rigui1 in a circadian fashion (Sun et al., 1997), but at ZT6, ZT12, ZT18 and ZT24 m-rigui2 is not detectable (data not shown). Taken together, m-rigui2 is expressed in the suprachiasmatic nucleus in a diurnal fashion, but differs from m-rigui1, in that it is not expressed in the pars tuberalis and the Purkinje neurons, in which m-rigui1 displayed a circadian expression pattern (Sun et al., 1997).

Figure 4:
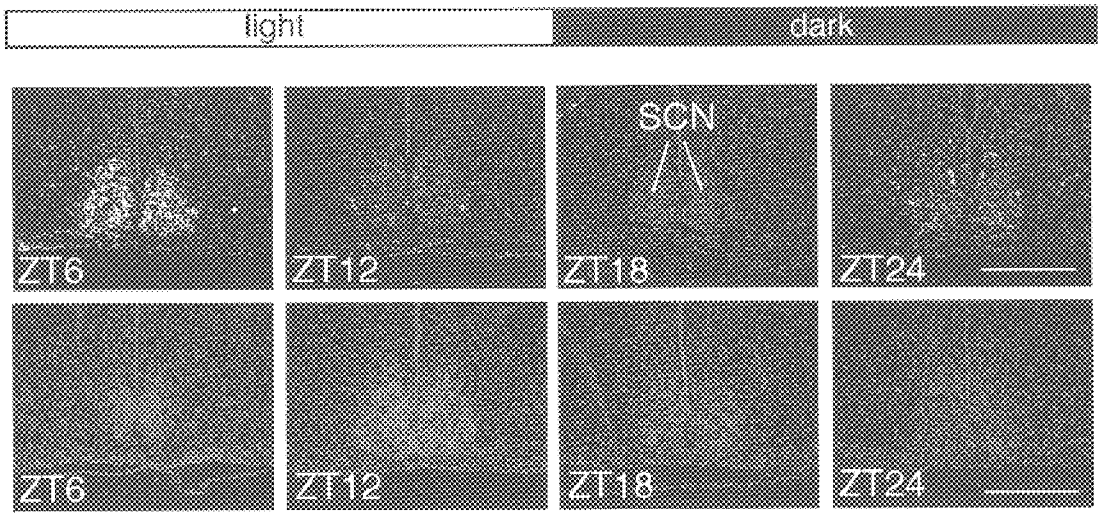
FIG. 4 shows the expression of m-rigui1 and m-rigui2 in the suprachiasmatic nucleus of male mice kept under a 12 hours light/12 hours dark cycle. Top row: the yellow signal shows the expression of m-rigui1 over 24 hours measured in 6 hours time intervals. Maximal expression is seen at ZT6. Bottom row: the red signal shows expression of m-rigui2 in adjacent sections. Maximal expression is seen at ZT12. Scale bar corresponds to 500 μm.

The time course of m-rigui1 and m-rigui2 expression in the suprachiasmatic nucleus was next compared using adjacent sections from the same animal. FIG. 4 shows data for ZT6, ZT12, ZT18, and ZT24 for m-rigui1 (top row, yellow signal) and m-rigui2 (bottom row, red signal). As previously reported (Sun et al., 1997; Tei et al., 1997), m-rigui1 is maximally expressed at about ZT6. m-rigui2 is also expressed at ZT6, but transcripts are more abundant at ZT12 (FIG. 4). Thus, there is a distinct difference in the temporal expression profile between the two m-rigui genes. However, there is an overlap in expression, and if transcript patterns reflect those of the proteins, it is possible that the m-rigui1 and m-rigui2 proteins interact in the suprachiasmatic nucleus through the PAS domain.

EXAMPLE 6

Figure 5:
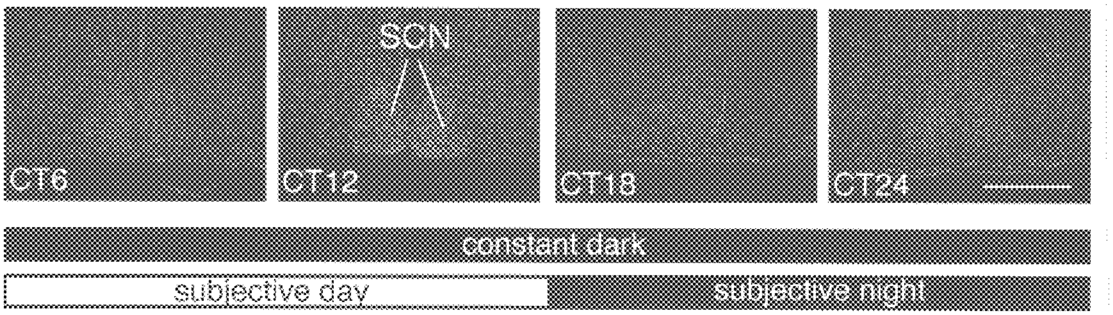
FIG. 5 shows the expression of m-rigui2 in the suprachiasmatic nucleus in male 129/SvEvBrd mice kept under free running conditions. Animals were transferred from a 12 hr light/12 hr dark cycle to constant darkness. The bar at the bottom of the figure indicates the subjective time. 72 hours after the transfer, animals were sacrificed every 6 hours at the times indicated in each of the panels. Strongest expression of m-rigui2 is seen at subjective circadian time CT12. Scale bar corresponds to 500 μm.

Circadian Expression of m-rigui2 in the SCN Persists Under Free-running Conditions To examine whether m-rigui2 continues to be expressed in a circadian fashion under constant darkness, 129/SvEvBrd males were transferred from a regular light/dark cycle to a dark/dark cycle. Starting 72 hours later, animals were sacrificed every six hours. m-rigui2 expression in the suprachiasmatic nucleus of these animals is depicted in FIG. 5. At subjective Circadian Time 6 (CT6), expression in the suprachiasmatic nucleus was low. At CT12, transcript levels had increased markedly. Thereafter, gene activity gradually declined to back-ground levels (CT18, CT24, FIG. 5). Thus, the diurnal expression pattern and the zenith of m-rigui2 expression is maintained under free-running conditions. This indicates that this gene has the characteristic of a circadian clock gene.

EXAMPLE 7

Entrainment of m-rigui2 Expression by Light

Figure 6:
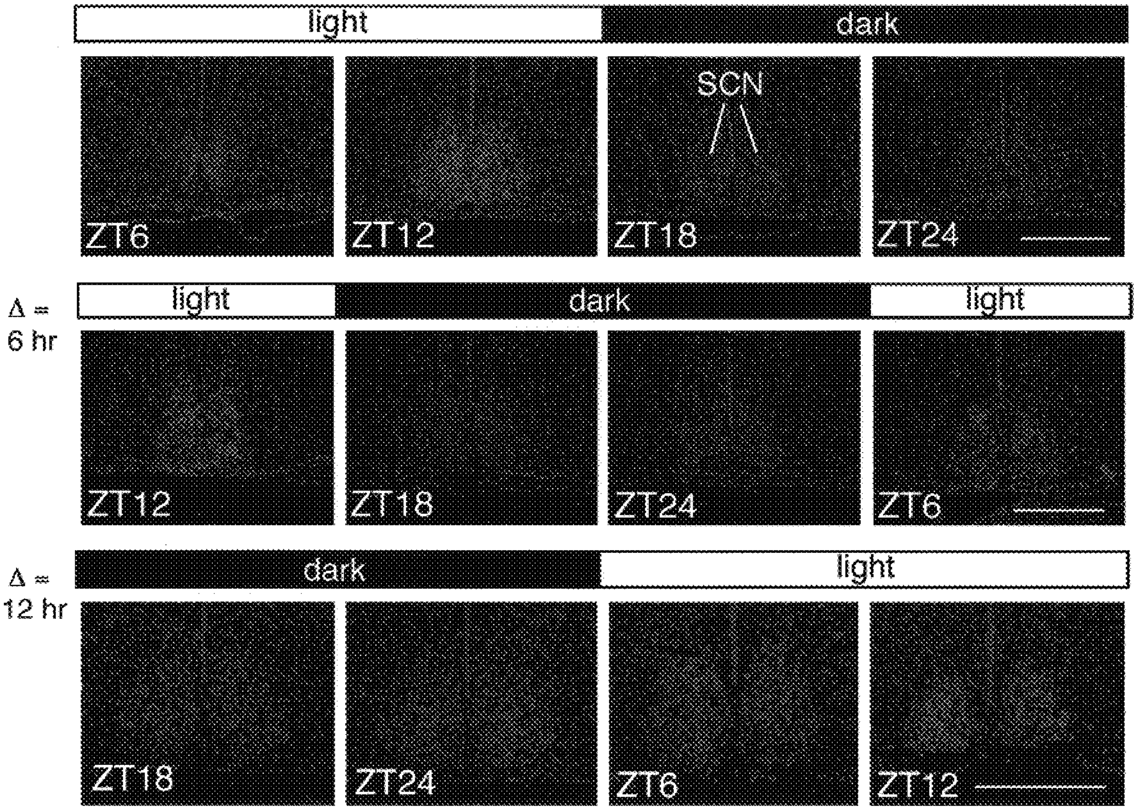
FIG. 6 shows the entrainment of m-rigui2 expression in the suprachiasmatic nucleus by a forward shift of the 12 hours light/12 hours dark cycle by 6 hours or 12 hours. Data are from C57BL/6 males. Top row: suprachiasmatic nucleus of a reference animal kept in the standard 12 hr light/12 hr dark cycle (zeitgeber light pattern is symbolized by the horizontal bar). Note maximal expression at ZT12. Middle row: Animals sacrificed 8 days following the 6 hour shift of the 12 hr light/12 hr dark cycle (zeitgeber light pattern is symbolized by the horizontal bar marked D=6 hours). High expression is seen at ZT12 indicating entrainment of m-rigui2 expression and acquisition of the new day/night cycle. Bottom row: Animals sacrificed after 14 days following the 12 hr shift of the 1 2 hr light/12 hr dark cycle (zeitgeber light pattern is symbolized by the horizontal bar marked D=12 hours). Maximal expression of m-rigui2 is entrained to the new ZT12. Scale bars correspond to 500 μm.

A change in the external light/dark cycle affects the expression pattern of circadian genes (Hardin et al., 1990; Saunders, et al., 1994; Crosthwaite et al., 1995; Sun et al., 1997). To test whether m-rigui2 transcript levels are affected by a shift in the light/dark cycle, C57BL/6 mice were transferred to a 12 hr light/12 hr dark cycle which had been advanced by either 6 or 12 hrs. Animals were analyzed on the day of the transfer to the new condition, and after 8 days (in the case of the 6 hr shift) or after 14 days (in the case of the 12 hr shift). An adjustment of maximal expression is clearly seen in FIG. 6. At day 0, that is prior to entrainment, expression peaked at ZT12 (FIG. 6, top row). After 8 days of entrainment, the 6 hr shift experiment again displayed maximal expression at ZT12, indicating that entrainment had been completed within this time period (FIG. 6, middle row). This is reminiscent of m-rigui1, whose entrainment is also completed within 8 days (Sun et al., 1997). Those animals that were subjected to a 12 hr shift and were analyzed by day 14 of treatment also adjusted their peak expression to the new ZT12 (FIG. 6, bottom row). From these data one can conclude that m-rigui2 expression could be synchronized to a changed light-dark cycle. Thus, this gene is entrainable like m-rigui1.

EXAMPLE 8 m-rigui1 but not m-rigui2 is Induced by a Pulse of Light at CT22

One could infer from the light entrainment experiments that the expression of both m-rigui genes is influenced by the light of the zeitgeber. However, these observations do not establish whether these two genes confer photic response to the circadian clock. The circadian regulatory gene period from Drosophila cannot be induced by a pulse of light (Zeng et al., 1996; Hunter-Ensor, M. et al., 1996) whereas frequency (frq), a circadian regulator in eurospora, is light inducible (Crosthwaite et al., 1995).

Classical physiologic studies establish that during the subjective night but not during the subjective day, a pulse of light can shift the phase of the circadian rhythms of mammals (Aschoff, 1969). This suggests that circadian regulators exist in mammals that respond to such light pulses. To examine whether m-rigui genes are turned on by a light pulse, animals were exposed to a 15 minute long light pulse at CT22, which falls into the subjective night period. Animals were sacrificed at 7, 15, 30, 60, and 120 minutes, whereby t=0 is the onset of light.

Figures 1, 7:
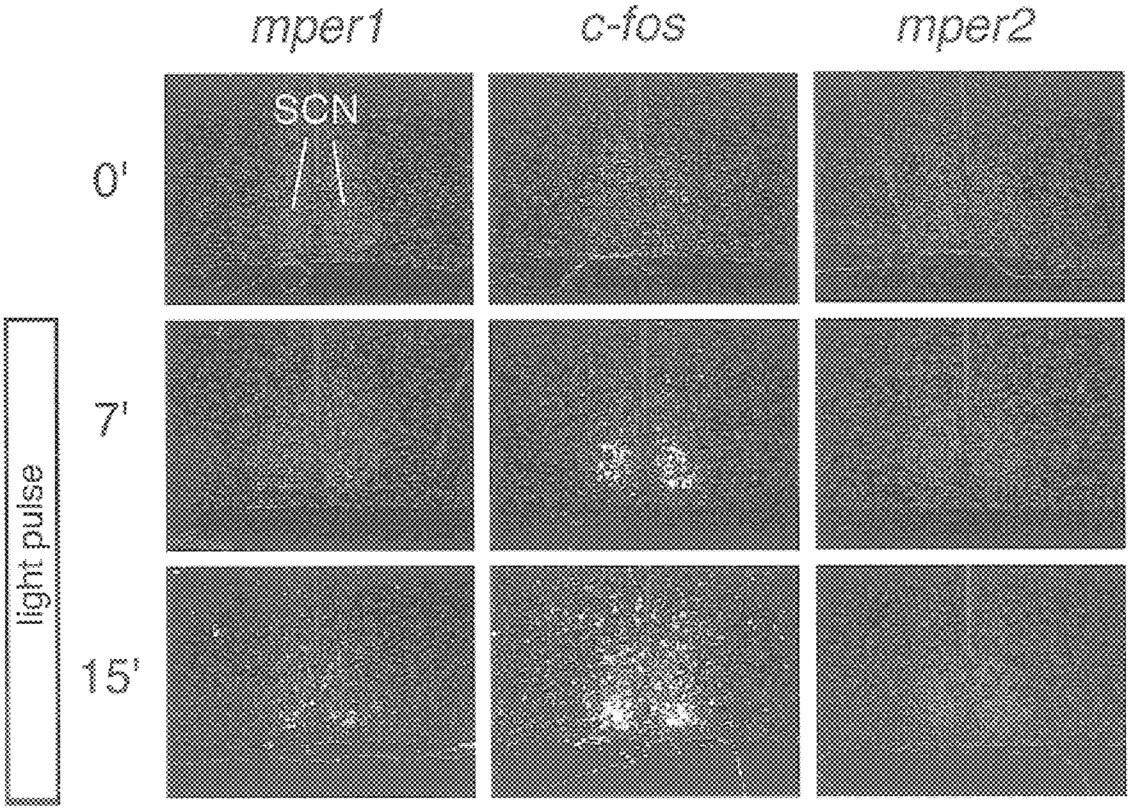
FIG. 7 shows the induction of m-rigui1 and c-fos but not m-rigui2 by a light pulse at CT22. m-rigui1 expression is shown in yellow (left column), c-fos in white (middle column) and m-rigui2 in red (right column). Sections in a row are adjacent to each other. The left vertical bar indicates the light pattern consisting of a 15 minute light pulse followed by a dark period. Note: mPer2 expression could still be induced by light at a different time period, e.g., at CT12 to CT18. Numbers indicate minutes from the start of the light pulse. Scale bar corresponds to 500 μm.
Figures 2, 7:
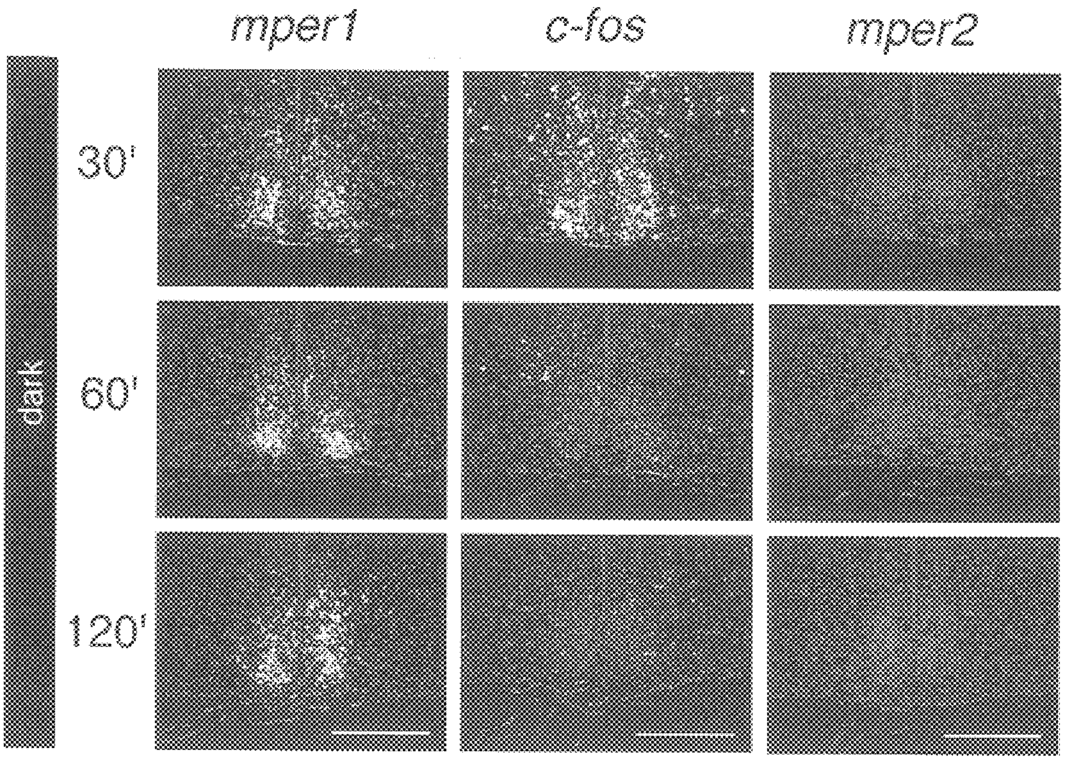

FIG. 7 shows the expression of m-rigui1, m-rigui2 and of c-fos, an immediate early gene that is rapidly induced by light during the subjective night (Aronin et al., 1990; Kornhauser et al., 1992). The left column in FIG. 7 illustrates that m-rigui1 expression is initiated towards the end of the light pulse, but becomes very strong by 30 minutes. m-rigui1 transcripts are initially confined to the ventrolateral region of the suprachiasmatic nucleus, but later m-rigui1 mRNA is found throughout the suprachiasmatic nucleus (FIG. 4, FIG. 7, 120 min time point). The suprachiasmatic nucleus of control animals that were not exposed to light but sacrificed at 120 min (CT24), did not exhibit any m-rigui1 expression (data not shown).

c-fos induction (center column in FIG. 7) is slightly more rapid than that of m-rigui1, with transcripts first detected at 7 minutes. However, expression is transient, declining after 30 minutes (Kornhauser et al., 1992). Similar to m-rigui1, c-fos transcripts are confined to the ventrolateral suprachiasmatic nucleus region. m-rigui2 behaves differently towards a light pulse. Unlike the two other genes, there is no increase in transcription throughout the 2 hour period of observation (FIG. 7, last column). Examination of a specimen after 4 hours following the light pulse (CT2), did not reveal significant m-rigui2 expression (same level of expression as CT24 control animal). This suggests, that at least as assessed by in situ hybridization, m-rigui2 expression is not induced by a pulse of light at CT22.

EXAMPLE 9

Light-inducibility of m-rigui2 (mPer2) correlates with phase delays.

Figure 8:
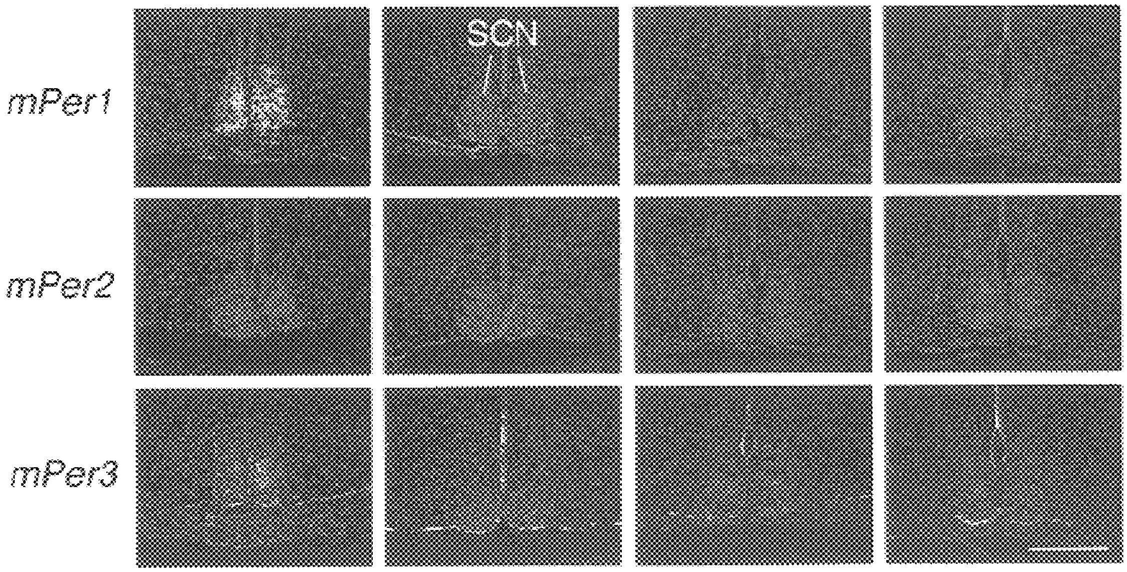
FIG. 8 shows the expression profile of mPer1 (m-rigui1), mPer2 (m-rigui2), and mPer3 in suprachiasmatic nuclei of mice kept under 12h light/12h dark conditions. Note the difference in peak expression of mPer1 and mPer2. Expression of mPer3 appears constant, although at ZT6, one of the two suprachiasmatic nucleus exhibits a slight increase in mPer3 signal. For each time point, adjacent sections of the same suprachiasmatic nucleus are shown. Scale bar: 500 μm.

There are significant differences in the temporal expression pattern and light inducibility of the m-rigui genes. FIG. 8 shows adjacent suprachiasmatic nucleus sections of the same mouse brain, and demonstrates that m-rigui1 and m-rigui2 transcript levels peak at different times, consistent with earlier reports (Albrecht et al., 1997b; Takumi et al., 1998a). In both cases, there are large changes in the level of gene expression. By contrast, in the case of mPer3, expression levels are low, and circadian regulation of expression is much less distinct (Takumi et al., 1998b; Zylka et al., 1998).

m-rigui2 is not (Albrecht et al., 1997b) or only very moderately (Zylka et al., 1998; Takumi et al., 1998b) induced by a light pulse during the phase advance period. By contrast, at CT14, m-rigui2 expression is rapidly activated by light. For the present study, the precise kinetics of m-rigui1 and m-rigui2 induction was determined for our experimental conditions. At CT14, both genes are induced within 15 to 30 minutes, beginning in those suprachiasmatic nucleus neurons that receive input from the retina via the retinohypothalamic tract (RHT, data not shown). Transcript levels are highest at one hour. Thereafter, mRNA levels decrease, and, by four hours both m-rigui genes are down-regulated to background levels.

EXAMPLE 10

Figure 9A:
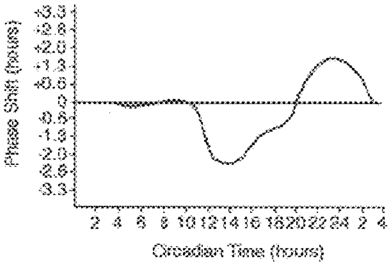
FIGS. 9A–9C show that induction levels of mPer2 (m-rigui2) reflect magnitude of behavioral phase shifting in response to light.

The Relationship Between m-rigui2 Induction by Light and the Delay Period of the PRC To investigate this relationship, the light inducibility of m-rigui2 between CT15 and CT22 at one hour intervals was examined. Since individual animals normally show variations in their circadian period ($\tau$) by as much as 30 minutes, $\tau$ for each individual animal was first determined using a circadian chamber. FIG. 9A shows the PRC for the C57BL/6 mouse strain (Schwartz and Zimmerman, 1990). The PRC consists of three regions: a non-responsive part which correspond to the subjective day, a delay region, and an advance region.

Figure 9B:
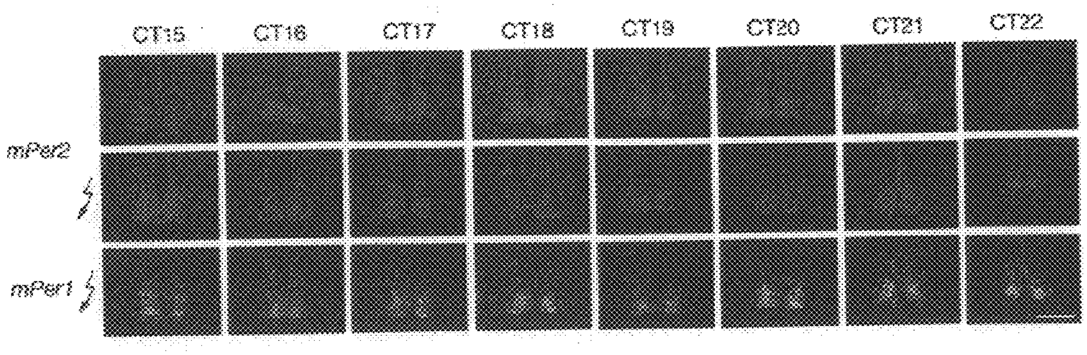

FIG. 9B illustrates the induction of m-rigui2 induction by a light pulse as visualized by in situ hybridization. For each data point, one free-running (in constant darkness) mouse was exposed for 15 minutes to 5000 lux of light. Animals were sacrificed 45 minutes later, at which time, m-rigui2 induction had reached a maximal level. Simultaneously, a control animal which was not pulsed with light was sacrificed. No determination of m-rigui2 induction at CT12, CT13 and CT14 was made, because the significant level of endogenous expression of this gene at these time points (Albrecht et al., 1997b) would mask induced expression. m-rigui2 is strongly induced at CT15 and CT16, whereas induction is markedly reduced at CT17 and CT18 (FIG. 2B). At CT19, induction is minimal, and at CT20 and thereafter, the suprachiasmatic nucleus of animals pulsed with light are devoid of m-rigui2 transcripts. In the same suprachiasmatic nucleus, m-rigui1 is induced by light, but at a constant level independent of the time when the pulse was applied (FIG. 9B). Qualitatively, the induction of m-rigui2 mirrors the PRC, in that strong induction correlates with large phase shifts. Strong m-rigui2 induction is seen at CT15 when phase delays are high, whereas light induction of m-rigui2 is modest at CT17 when phase delays are also modest. The low light induction of m-rigui2 seen at CT19 correlates with the minor phase delays seen at this time. Finally, at the transition point between delays and advances and during the phase advance period, no m-rigui2 induction can be detected.

Figure 9C:
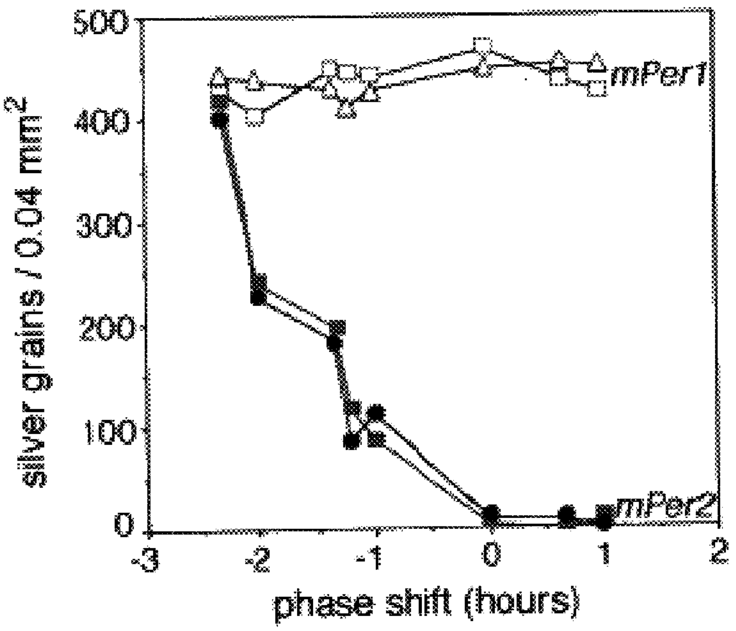

FIG. 9C shows the relationship of m-rigui1 and m-rigui2 to the phase delay. The graphs are based on silver grain densities determined from the in situ hybridization experiments as exemplified in FIG. 9B. It can be seen that the extent of light-inducibility of m-rigui2 correlates with the amount of phase delay, while m-rigui1 inducibility levels are invariant. In summary, the light inducibility of m-rigui2 is restricted to the delay period of the PRC and m-rigui2 transcript levels are proportional to the magnitude of the phase shifts.

EXAMPLE 11 m-rigui2 inducibility by a double light pulse demonstrates rapid resetting of the circadian clock during the delay period of the PRC.

Wheel-running experiments suggest that the mammalian circadian clock is rapidly reset by light (Hastings et al., 1996; Sharma and Chandrashekaran, 1997). Specifically, these studies show that two light pulses (one at CT14 the second at CT16) lead to a significantly increased phase delay when compared with a single light pulse given at CT14. Such large composite phase delays are suggestive of clock resetting occuring between the two light pulses.

The molecular basis of this phenomenon was addressed by studying the inducibility of m-rigui2 by single and double light pulse treatments. The PRC shown in FIG. 9A predicts that a single light pulse given at CT14 will result in a phase delay of approximately ~2.5 hours. Thus, theoretically, if the clock is rapidly reset in response to the pulse, a second light pulse administered two hours later would not fall at CT16 but at CT13.5. As can be seen in FIG. 10, a single light pulse given at CT14 resulted in a high level of m-rigui2 expression when the suprachiasmatic nucleus was analyzed 2 hours later, but signal strength decreased to background by 4 hours after the pulse was given. However, when a second light pulse was given 2 hours after the initial light pulse, the level of m-rigui2 expression was sustained for at least two additional hours. If the clock had not reset and the seconds pulse would thus have fallen at CT16, the induction would have been weaker (see FIG. 9B). Of note, a single 30 minute light pulse administered at CT14 was not capable of sustaining m-rigui2 expression through the same period, indicating that it is the temporal pattern and not the total duration of the pulse that matters. Thus the augmentation of the phase delay caused by a double pulse (Hastings et al., 1996; Sharma and Chandrashekaran, 1997) is reflected in sustained expression of m-rigui2 for a substantially longer time than that seen with a single light pulse.

A single light pulse given at CT18 induced m-rigui2 only weakly (FIG. 11). Assuming that this first pulse resets the clock by 1 to 2 hours (FIG. 9A), the second pulse given two hours later would theoretically encounter the clock not at Cr20 but closer to CT18, at which time m-rigui2 is light-inducible (FIG. 9B). As can be seen in FIG. 11, the double pulse at these times results in significant m-rigui2 expression 1 h after the second pulse. This implies that the clock had been reset by the first pulse. In the control experiment in which the second light pulse was omitted, no expression of m-rigui2 was observed (FIG. 11). Taken together, the double pulse experiments indicate that the first pulse has reset the clock and that this resetting occurred in 2 hours or less.

Light pulses applied during the late subjective night advance the clock (Pittendrigh and Daan, 1976). Consistent with this behavioral data, and the notion that m-rigui2 encodes a phase delay factor, m-rigui2 was not induced either by a single or by a double light pulse in the late subjective night (CT 22 to CT24, data not shown). This contrasts greatly with m-rigui1 as well as c-fos and other immediate-early genes that are all rapidly inducible even by a single pulse during the advance phase (Rusak et al., 1990; Guido et al., 1996; Albrecht et al., 1997b). Taken together, this data shows that m-rigui2 induction by light is confined to the delay phase, implicating m-rigui2 in the delay resetting mechanism of the circadian clock.

DISCUSSION

In many instances, several vertebrate homologs have been found for each Drosophila gene involved in signal transduction. Recent work has identified a mouse gene encoding a putative circadian protein named either m-rigui1 (Sun et al., 1997) or m-per (Tei et al., 1997). In addition, a cDNA sequence (KIAA0347) that encodes a protein with significant homology to the Drosophila period protein has been reported (Nagase et al., 1997). Sun et al., 1997 noted that KIAA0347 encodes a protein homologous to human RIGUI. The putative functions of KIAA0347 are not known which led to a search for the corresponding mouse homolog.

A RT-PCR strategy was used to isolate this mouse homolog, which has been designated as m-rigui2. m-rigui2 is expressed in a circadian pattern in the suprachiasmatic nucleus, maintains expression under free-running conditions (constant darkness) and can be synchronized to the cycle of an external light source (entrainment). These are hallmarks of a circadian gene. Expression of m-rigui1 and m-rigui2 in the suprachiasmatic nucleus is overlapping but not synchronous. m-rigui1 transcripts culminate approximately four hours prior to that of m-rigui2. In the suprachiasmatic nucleus of animals exposed to a pulse of light begins transcription of m-rigui1 within 7 to 15 minutes. At CT22, m-rigui2 is directly not light-inducible and thus behaves more like the Drosophila per gene, which is not inducible by light (Zeng et al., 1996; Hunter-Ensor et al., 1996).

The in situ hybridization analyses of the suprachiasmatic nucleus of animals kept in a 12 hr light/12 hr dark cycle, constant darkness, or under entrainment conditions, show that m-rigui1 is maximally expressed at ZT/CT6, whereas m-rigui2 lags behind by approximately 4 hrs. However, m-rigui2 is expressed at ZT/CT6 and thus the neurons of the suprachiasmatic nucleus may contain transcripts from both genes. Assuming that the temporal expression pattern of the corresponding proteins mirrors that of the transcripts, m-rigui1 and m-rigui2 proteins may interact directly. The m-rigui proteins have highly homologous PAS domains (61% identity), and others have provided evidence that such PAS domains mediate the interaction between different PAS domain-containing proteins and also the interaction with other transacting factors (Huang et al., 1993; Lindebro et al., 1995; Zelzer et al., 1997). It is thus possible that m-rigui1 and 2 form heterodimers with each other and with other proteins such as clock. Clock transcripts are broadly expressed in the brain including the suprachiasmatic nucleus (King et al., 1997). Several tissues, like testis and skeletal muscle, express m-rigui1 and not m-rigui2. In these tissues, m-rigui1 may function independently of m-rigui2, possibly in conjunction with other PAS domain-containing proteins.

The response of the mammalian circadian clock to light is complex and little understood. The activation of photoreceptors in the retina generates signals that are transduced to the suprachiasmatic nucleus through the retinohypothalamic tract (RHT). In the retinorecipient area of the suprachiasmatic nucleus, the region into which the retinohypothalamic tract projects (Hendrickson et al., 1972; Moore and Lenn, 1972; Johnson et al., 1988), releases glutamate evoking a calcium influx which may activate the nitric oxide signaling cascade (Schwartz et al., 1995; Hastings et al., 1995; Ding et al., 1994). The molecular targets of this signal transduction process are one or several proteins of the circadian clock. The properties of the rigui gene products qualify them as putative circadian clock components and as such they are potential targets of the signal mediated through the retinohypothalamic tract.

m-rigui1 is induced by a pulse of light within 15 minutes after turning on the light source. Induction of m-rigui1 by light initially occurs in a small number of ventrally located cells, and by 30 minutes m-rigui1 transcripts are found in a broader but still ventral region of the suprachiasmatic nucleus. This is the retinorecipient area (Moore and Lenn, 1972; Hendrickson et al., 1972; Johnson et al., 1988) also characterized by the expression of several neuropeptides (Card and Moore, 1991). Between 60 and 120 minutes, other dorsal neurons also initiate m-rigui1 transcription. This broadening of expression eventually leads to the uniform expression encompassing the whole suprachiasmatic nucleus.

The induction of m-rigui1 by a pulse of light provided at CT22 occurs rapidly. Transcriptional activation of immediate early genes such as c-fos and junB respond slightly faster, but on a similar time scale (Kornhauser et al., 1992). However, unlike m-rigui1, none of these immediate early genes shows a circadian expression pattern. At the time of initiation of m-rigui1 expression around ZT4 (Tei et al., 1997), c-fos is not inducible by light (Kornhauser et al., 1992). frequency (frq) a circadian clock gene in *Neurospora crassa* is turned on by light after 5 minutes, and achieves maximal induction by 15 minutes (Crosthwaite et al., 1995), a time scale similar to that seen with m-rigui1. A difference between frq and m-rigui1 is that the message levels of frq begin to decline after 15 minutes and are close to background levels by 2 hours (Crosthwaite et al., 1997).

The expression of m-rigui1 and m-rigui2 is entrainable by light. The molecular basis of entrainment may involve m-rigui1, because this gene is rapidly light-inducible and encodes a putative transcription factor. A possible model is that light evokes a signal in the retina, which is transduced through the retinohypothalamic tract to the ventral portion of the suprachiasmatic nucleus, the region where m-rigui1 is first transcribed. This sets up a positive autoregulatory loop of m-rigui1 expression. This initial expression establishes a condition in which light is no longer required to maintain m-rigui1 expression. As shown herein, m-rigui1 expression continues hours after the light pulse is terminated. m-rigui1 would then activate the m-rigui2 gene, which is not itself light-inducible. The 4 hour time delay between m-rigui1 and m-rigui2 expression could be explained by a requirement of a threshold concentration of m-rigui1 protein to turn on m-rigui2.

mPer2 mediates clock resetting during the delay phase of the circadian cycle.

The three mPer (m-rigui1, m-rigui2 and mPer3) genes differ from each other in several respects. Most importantly, the three genes differ in their peak expression times and their responses to light. m-rigui1 and m-rigui2 are inducible during the phase delay period, but only m-rigui1 is significantly light inducible during the phase advance period (Albrecht et al., 1997b; Zylka et al., 1998). This observation prompted examination of the function of m-rigui2 during the delay phase of the circadian cycle. There is a direct relationship between the level of m-rigui2 induction and the magnitude of clock resetting as determined by locomotor activity. During the early subjective night (CT14), a light pulse induced m-rigui2 strongly, but the capacity of the m-rigui2 gene to respond to such a pulse gradually diminished and the gene became refractory to induction during the phase advance period (CT20 to CT24; Zylka et al., [1998] reported a weak m-rigui2 induction at CT 23 and 24). We found that the level of m-rigui2 induction was proportional to the amount of phase delay caused by a light pulse at a particular CT. Typically in C57BL/6 mice, the strain of mice we studied, pulses at around CT14 induced m-rigui2 strongly, causing a delay of approximately −2.5 hours (Schwartz and Zimmerman, 1990). By contrast, a pulse at CT18 evoked a weak m-rigui2 induction and a smaller delay. It thus appears that the degree by which the clock is turned back by a light pulse is reflected in the level of induced m-rigui2 mRNA, and therefore, presumably, by the level of induced mPer2 (m-rigui2) protein.

If induced m-rigui2 levels reflect the magnitude of clock resetting, a double pulse which leads to more persistent m-rigui2 expression than a single pulse, should increase the magnitude of the resetting. Indeed, behavioral studies in hamsters (Hastings et al., 1996), and mice (Sharma and Chandrashekaran, 1997; Hastings et al., 1996) have shown that a double light pulse applied during the delay phase had exactly this effect. For example in field mice, a single light pulse applied at CT14 caused a delay of about 2 hours, while a double pulse (CT14 and then CT16) resulted in a 3.5 hour delay (Sharma and Chandrashekaran, 1997). Since m-rigui1 is light-inducible throughout the night, and induction does not vary with the circadian time, expression of this gene does not differentiate between the phase delay and phase advance periods. Hence, m-rigui1 is less likely to play a prominent role in the phase delay mechanism.

How would a light-induced m-rigui2 (mPer2) protein reset the circadian clock? One can envision the following model: normally, m-rigui2 expression peaks at around CT12 and then gradually disappears and is no longer detected by CT17. A pulse of light applied at CT14 will cause a large increase in m-rigui2 levels. High endogenous levels are typical at CT12 and thus the clock is reset towards this time. A pulse applied around CT18 induces significantly less m-rigui2 and low concentrations of m-rigui2 are characteristic for later CTs. Although the clock still resets, it does so by a more modest amount. This model thus proposes that during the delay phase of the circadian cycle, m-rigui2 protein abundance determines the circadian time and that the m-rigui2 gene product is involved in the clock resetting mechanism.

Regulation of m-rigui2 expression by double light pulses suggests a rapid resetting of the mammalian clock.

Locomotor activity measurements of hamster and mice suggests that the mammalian clock is reset within a few hours (Hastings et al., 1996; Sharma and Chandrashekaran, 1997). However, at the present time, none of the genes implicated in the clock itself have been used to address the issue of resetting rates of the mammalian clock. A model in which m-rigui2 abundance defines the circadian time during the delay phase of the circadian cycle was outlined. One facet of this model is that a light pulse that rapidly induces m-rigui2 would shift the CT to an earlier CT. The double light pulse protocol shed light on this issue and allows one to determine the time frame within which resetting occurs. A light pulse given at CT14 quickly induces m-rigui2. A second pulse was then applied two hours later. If the clock had progressed and not reset, it would be at CT16. Thus a second pulse hitting the suprachiasmatic nucleus would induce m-rigui2 only moderately. However, the second pulse resulted in strong induction, with m-rigui2 transcripts being abundant even two hours after the application of the second pulse. This indicates that the first pulse had reset the clock, and that this had occurred within the two hour period between the two pulses. The same conclusion can be drawn from the CT18/20 double-pulse data. In this case, a pulse at CT18 evoked a weak induction of m-rigui2. If the clock had been unaffected by this pulse, then a second pulse applied two hours after the initial pulse, would meet the clock at CT20, at which time a pulse would have no inductive effect on m-rigui2 expression. However, the second pulse markedly induced m-rigui2 expression, again suggesting that within the two hour interval, the clock had reset to an earlier time. This demonstrates that the CT had been reset in response to light within two hours. This data thus provides a direct molecular readout of the clock resetting rate during the phase delay period and lend credence to behavioral data that have addressed the same issue and arrived at the same time frame (Hastings et al., 1996; Sharma and Chandrashekaran, 1997).

What could be the benefit of having multiple m-per (m-rigui) genes? These genes are clearly not redundant: they are maximally expressed at different times of the circadian cycle, they differ with regard to their response to light, and there are marked differences in the tissue expression profile. Thus these genes must have different regulatory regions, a diversity which would allow response to a broader spectrum of input cues, or perhaps interact different downstream components. Thus the m-rigui1 regulatory region may respond primarily to light, while the regulatory region of m-rigui2 could respond to hormonal or other signals. Thus diverse input signals would result in the biosynthesis of two similar proteins that, due to their relatedness, can drive the same signalling pathways.

The following references were cited herein:

Albrecht, U., Eichele, G., Helms, J. A., and Lu, H. (1997a). Visualization of gene expression patterns by in situ hybridization. *Molecular and Cellular Methods in Developmental Toxicology*, Boca Raton, CRC Press, Inc. 23–48.

Albrecht, U., Sun, Z. S., Eichele, G. and Lee, C. C. (1997b). A differential response of two putative mammalian circadian regulators to light. Cell 91, 1055–1064.

Albrecht, U., Lu, H.-C., Revelli, J.-P., Xu, X.-C., Lotan, R. and Eichele, G. (1998). Studying gene expression on tissue sections using in situ, hybridization. *Human Genome Methods*. Boca Raton, CRC Press, Inc. 93–120.

Altschul, S. F., Gish, W., Miller, W., Myers, E. W., Lipman, D J. (1990). Basic local alignment search tool. J. Mol. Biol. 215, 403–410.

Aronin, N., Sagar, S. M., Sharp, F. R. and Schwartz, W. J. (1990). Light regulates expression of a fos-related protein in rat suprachiasmatic nuclei. Proc. Natl. Acad. Sci. USA 87, 5959–5962.

Aschoff, J. (1969). Desynchronization and resynchronization of human circadian rhythms. Aerosp. Med. 40, 844–849.

Bargiello, T. A., Jackson, F. R. and Young, M. W. (1984). Restoration of circadian behavioural rhythms by gene transfer in Drosophila. Nature 312, 752–754.

Card, J. P. and Moore, R. Y. (1991). The organization of visual circuits influencing the circadian activity of the suprachiasmatic nucleus. *Suprachiasmatic nucleus: The mind's clock*. New York, Oxford University Press. 51–76.

Citri, Y., Colot, H. V., Jacquier, A. C., Yu, Q., Hall, J. C., Baltimore, D. and Rosbash, M. (1987). A family of unusually spliced biologically active transcripts encoded by a Drosophila clock gene. Nature 326, 42–47.

Crosthwaite, S. C., Loros, J. J. and Dunlap, J. C. (1995). Light induced resetting of a circadian clock is mediated by a rapid increase infrequency transcript. Cell 81, 1003–1012.

Crosthwaite, S. K., Dunlap, J. C. and Loros, J. J. (1997). Neurospora wc-1 and wc-2: Transcription, photoresponses, and the origins of circadian rhythmicity. Science 276, 763–769.

Ding, J. M., Chen, D., Weber, E. T., Faiman, L. E., Rea, M. A. and Gillette, M. U. (1994). Resetting the biological clock: mediation of nocturnal circadian shifts by glutamate and NO. Science 266, 1713–1717.

Dunlap, J. C. (1996). Genetic and molecular analysis of circadian rhythms. Annu. Rev. Genet. 30, 579–601.

Guido, M. E., Rusak, B. and Robertson, H. A. (1996). Spontaneous circadian and light induced expression of junB mRNA in the hamster suprachiasmatic nucleus. Brain Res. 732, 215–222.

Hall, J. C. (1990). Genetics of circadian rhythms. Annu. Rev. Genet. 24, 659–597.

Hall, J. C. and Rosbash, M. (1993). Oscillating molecules and how they move circadian clocks across evolutionary boundaries. Proc. Natl. Acad. Sci. USA 90, 5382–5383.

Hall, J. C. (1996). Are cycling gene products as internal zeitgebers no longer the zeitgeist of chronobiology. Neuron 17, 799–802.

Hardin, P. E., Hall, J. C. and Rosbash, M. (1990). Feedback of the Drosophila period gene product on circadian cycling of its messenger RNA levels. Nature 343, 536–540.

Hastings, M. H., Ebling, F. J., Grosse, J., Herbert, J., Maywood, E. S., Mikkelsen, J. D and Sumova, A. (1995). Immediate-early genes and the neural bases of photic and nonphotic entrainment. Ciba Found. Symp. 183, 175–189.

Hastings, M. H., Best, J. D., Ebling, F. J. P., Maywood, E. S., McNulty, S., Schurov, I., Selvage, D., Sloper, P. and Smith, K. L. (1996). Entrainment of the circadian clock. *Progress in Brain Research*. Amsterdam, Elsevier Science BV. 147–174.

Hendrickson, A. E., Wagoner, N. and Cowan, W. M. (1972). An autoradiographic and electron microscopic study of retinohypothalamic connections. Z. Zellforsch. 135, 1–36.

Huang, Z. J., Edery, I. and Rosbash, M. (1993). PAS is a dimerization domain common to Drosophila period and several transcription factors. Nature 364, 259–262.

Hunter-Ensor, M., Ousely, A., Sehgal, A. (1996). Regulation of Drosophila protein timeless suggests a mechanism for resetting the circadian clock by light. Cell, 84, 677–685.

Johnson, R. F., Morin, L. P. and Moore, R. Y. (1988). Retinohypothalamic projections in hamster and rat demonstrated using cholera toxin. Brain Res. 462, 301–312.

King, D. P., Zhao, Y., Sangoram, A. M., Wilsbacher, L. D., Tanaka, M., Antoch, M. P., Steeves, T. D. L., Vitaterna, M. H., Kornhauser, J. M., Lowery, P. L., Turek, F. W. and Takahashi, J. S. (1997). Positional cloning of the mouse circadian Clock gene. Cell 89, 641–653.

Konopka, R. J. and Benzer, S. (1971). Clock mutants of *Drosophila melanogaster*. Proc. Nat. Acad. Sci. USA 68, 2112–2116.

Kornhauser, J. M., Nelson, D. E., Mayo, K. E. and Takahashi, J. S. (1992). Regulation of jun-B messenger RNA and AP-1 activity by light and a circadian clock. Science 255, 1581–1584.

Lindebro, M. C., Poellinger, L. and Whitelaw, M. L. (1995). Protein-protein interaction via PAS domains: Role of the PAS domain in positive and negative regulation of the bHLH/PAS dioxin receptor-Arnt transcription factor complex. EMBO J. 14, 3528–3539.

Ma, P. C., Rould, M. A., Weintraub, H. and Pabo, C. O. (1994). Crystal structure of MyoD bHLH domain-DNA complex: perspectives on DNA recognition and implications for transcriptional activation. Cell 77, 451–459.

Moore, R. Y. (1995). Organization of the mammalian circadian system. CIBA Found. Symp. 183, 88–99.

Moore, R. Y. and Lenn, N. J. (1972). A retinohypothalamic projection in the rat. J. Comp. Neurol. 146, 1–14.

Nagase, T., Ishikawa, K., Nakajima, D., Ohira, M., Seki, N., Miyajima, N., Tanaka, A., Kotani, H., Nomura, N. and Ohara, O. (1997). Prediction of the coding sequences of unidentified human genes. VII. The complete sequences of 100 new cDNA clones from brain which can code for large proteins in vitro. DNA Res 4, 141–150.

Pittendrigh, C. S. and Daan, S. (1976). A functional analysis of circadian pacemakers in nocturnal rodents. V. Pacemaker strucuture: A clock for all seasons. J. Comp. Physiol. 106, 333–355.

Pittendrigh, C. S. (1993). Temporal organization: reflections of a Darwinian clock-watcher. Annu. Rev. Physiol. 55, 16–54.

Ponting, C. P. and Aravind, L. (1997). PAS: a multifunctional domain family comes to light. Curr. Biol. 7, R674–R677.

Ralph, M. R., Foster, R. G., Davis, F. C. and Menaker, M. (1990). Transplanted suprachiasmatic nucleus determines circadian period. Science 247, 975–978.

Reppert, S. M. and Sauman, I. (1995). period and timeless tango: a dance of two clock genes. Neuron 15, 983–986.

Rusak, B., Robertson, H., Wisden, W. and Hunt, S. P. (1990). Light pulses that shift rhythms induce gene expression in the suprachiasmatic nucleus. Science 248, 1237–1240.

Sambrook, J., Fritsch, E. F. and Maniatis, T. (1989). Molecular Cloning. A Laboratory Manual. Cold Spring Harbor, N.Y.

Saunders, D. S., Gillanders, S. W. And Lewis, R. D. (1994). Light pulse phase response curves for the locomotor activity rhythm in period mutants. J. Insect Physiol. 40, 957–968.

Schwartz, W. J. and Zimmerman, P. (1990). Circadian timekeeping in BALB/c and C57BL/6 inbred mouse strains. J. Neurosci. 10, 3685–3694.

Schwartz, W., Aronin, N., Takeuchi, J., Bennett, M. and Peters, R. (1995). Towards a molecular biology of the suprachiasmatic nucleus: photic and temporal regulations of c-fos gene expression. Semin. Neurosci. 7, 53–60.

Sehgal, A., Price, J. L., Man, B. and Young, M. W. (1994). Loss of circadian behavioral rhythms and per RNA oscillations in the Drosophila mutant timeless. Science 263, 1603–1606.

Sharma, V. K. and Chandrashekaran, M. K. (1997). Rapid phase resetting of a mammalian circadian rhythm by brief light pulses. Chronobiol. Int. 14, 537–548

Shearman, L. P., Zylka, M. J., Weaver, D. R., Kolakowski, L. F. and Reppert, S. M. (1997). Two period homologs: circadian expression and photic regulation in the suprachiasmatic nuclei. Neuron 19,1261–1269.

Siwicki, K. K., Schwartz, W. J. and Hall, J. C. (1992). An antibody to the Drosophila period protein labels antigens in the suprachiasmatic nucleus of the rat. J. Neurogenetics 8, 33–42.

Smith, R. F. and Smith, T. F. (1992). Pattern-induced multi-alignment (PIMA) algorhythm employing secondary structure-dependent gap penalties for comparative protein modelling. Prot. Engineering 5, 35–41.

Sun, Z. S., Albrecht, U., Zhuchenko, O., Bailey, J., Eichele, G. and Lee, C. C. (1997). Rigui a putative mammalian ortholog of the Drosophila period gene. Cell 90, 1003–1011.

Takahashi, J. S. (1995). Molecular neurobiology and genetics of circadian rhythms in mammals. Ann. Rev. Neurosci. 531–553.

Takumi, T., Matsubara, C., Shigeyoshi, Y., Taguchi, K., Yagita, K, Maebayashi, Y., Sakakida, Y., Okumura, K., Takashima, N. and Okamura, H. (1998a). A new mammalian period gene predominatly expressed in the suprachiasmatic nucleus. Genes to Cells 3, 167–176.

Takumi, T., Taguchi, K., Miyake, S., Sakakida, Y., Takashima, N., Matsubara, C., Maebayashi, Y., Okumura, K., Takekida, S., Yamamoto, S., Yagita, K., Yan, L., Young, M. W. and Okamura, H. (1998b). A light-independent oscillatory gene mPer3 in mouse SCN and OVLT. EMBO J. 17, 4753–4759.

Tei, H., Okamura, H., Shigeyoshi, Y., Fukuhara, C., Ozawa, R., Hirose, M. and Sakaki, Y. (1997). Ciradian oscillation of a mammalian homolog of the Drosophila period gene. Nature 389, 512–516.

Zelzer, E., Wappner, P. and Shilo, B. Z. (1997). The PAS domain confers target gene specificity of Drosophila bHLH/PAS proteins. Genes & Dev. 11, 2079–2089.

Zeng, et al., (1996). Nature 380, 129–135.

Zylka, M. J., Shearman, L. P., Weaver, D. P. and Reppert, S. M. (1998). Three period homologs in mammals: differential light responses in the suprachiasmatic circadian clock and oscillating transcripts outside of brain. Neuron 20, 1103–1110.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. Isolated and purified m-rigui2 protein, wherein said m-rigui2 protein has the amino acid sequence SEQ ID No. 3, and wherein said DNA is coded for by DNA selected from the group consisting of:

(a) isolated DNA which encodes an m-rigui2 protein;

(b) isolated DNA which hybridizes to isolated DNA of (a) above at conditions consisting of hybridization in 5×SSC, 1% SDS at 65° C. followed by washing at 65° C. with SSC ranging in concentration from 1× to 0.1× containing 0.1% SDS, wherein said DNA encodes an m-rigui2 protein; and (c) isolated DNA differing from the isolated DNAs of (a) and (b) above in codon sequence due to the degeneracy of the genetic code, and which encodes an m-rigui2 protein.

2. Isolated DNA encoding an m-rigui2 protein, wherein said m-rigui2 protein has the amino acid sequence SEQ ID No. 3.

3. The DNA of claim 2, wherein said DNA is mouse DNA.

4. The DNA of claim 3, wherein said DNA has the sequence shown in SEQ ID No. 4.

5. The DNA of claim 2, wherein said DNA encodes a protein having the sequence shown in SEQ ID No. 3.

6. A vector capable of expressing the DNA of claim 2 adapted for expression in a recombinant cell and regulatory elements necessary for expression of the DNA in the cell.

7. A host cell transfected with the vector of claim 6, said vector expressing a m-rigui2 protein.

8. The host cell of claim 7, wherein said cell is selected from group consisting of bacterial cells, mammalian cells, plant cells and insect cells.

9. An isolated DNA encoding a protein having m-rigui2 activity, wherein said DNA hybridizes to isolated DNA comprising the nucleotide sequence depicted SEQ ID NO:4, wherein said hybridization conditions consist of hybridization in 5×SSC, 1% SDS at 65° C. followed by washing at 65° C. with SSC ranging in concentration from 1× to 0.1× and containing 0.1% SDS.

10. A method of detecting expression of the DNA of claim 2, comprising the steps of:

(a) contacting mRNA obtained from a cell with a labeled hybridization probe; and (b) detecting hybridization of the probe with the mRNA.

11. The method of claim 10, wherein said probe consists of a portion of the DNA of SEQ ID No. 4.

* * * * *

UNITED STATES PATENT AND TRADEMARK OFFICE
CERTIFICATE OF CORRECTION

PATENT NO. : 6,210,923 B1
APPLICATION NO. : 09/220641
DATED : April 3, 2001
INVENTOR(S) : Cheng-Chi Lee et al.

It is certified that error appears in the above-identified patent and that said Letters Patent is hereby corrected as shown below:

Column 1, line 11, "government" should read --Government--.

Column 1, line 19, "squencing" should read --sequencing--.

Column 1, line 27, "period (per)" should be --italicized--.

Column 1, line 55, "per" should be italicized.

Column 1, line 55, "timeless" should be italicized.

Column 1, line 56, "(tim)" should be italicized.

Column 1, line 59, "per" should be italicized.

Column 1, line 60, "(tim)" should be italicized.

Column 1, line 61, "per" should be italicized.

Column 1, line 62, "per" should be italicized.

Column 1, line 62, "per" should be italicized.

Column 2, lines 14-15, "Drosophila per" should be italicized.

Column 2, line 19, "h-per" should be italicized.

UNITED STATES PATENT AND TRADEMARK OFFICE

CERTIFICATE OF CORRECTION

PATENT NO. : 6,210,923 B1
APPLICATION NO. : 09/220641
DATED : April 3, 2001
INVENTOR(S) : Cheng-Chi Lee et al.

It is certified that error appears in the above-identified patent and that said Letters Patent is hereby corrected as shown below:

Column 2, lines 19-20, "Drosophila per" should be --italicized--.

Column 2, line 20, "m-rigui/m-per" should be --italicized--.

Column 2, line 28, please insert a period after "1998)".

Column 2, line 30, "squencing" should read --sequencing--.

Column 4, line 12, please remove the space from between "1" and "2".

Column 5, line 64, "acid" should read --acids--.

Column 6, line 5, "nomeclature" should read --nomenclature--.

Column 7, line 11, "specicif" should read --specific--.

Column 8, line 39, "phophory1ation" should read --phosphorylation--.

Column 9, line 34, "quantitiy" should read --quantity--.

Column 14, line 15, "a" should read --an--.

Column 22, line 27, "were" should read --was--.

Column 22, line 28, "was" should read --were--.

Column 24, line 4, "m-rigui2" should read --M-rigui2--.

Column 24, line 39, "m-rigui2" should read --M-rigui2--.

Column 24, line 46, "is" should read --are--.

UNITED STATES PATENT AND TRADEMARK OFFICE

CERTIFICATE OF CORRECTION

PATENT NO. : 6,210,923 B1
APPLICATION NO. : 09/220641
DATED : April 3, 2001
INVENTOR(S) : Cheng-Chi Lee et al.

It is certified that error appears in the above-identified patent and that said Letters Patent is hereby corrected as shown below:

Column 25, line 21, "eurospora" should read --Neurospora--.

Column 25, line 46, "c-fos" should read --C-fos--.

Column 26, line 52, "are" should read --is--.

Column 30, line 47, "suggests" should read --suggest--.

Column 32, line 52, "messanger" should read --messenger--.

Column 33, line 9, "strucuture" should read --structure--.

Column 34, line 15, "predominatly" should read --predominantly--.

Column 34, line 25, "Ciradian" should read --Circadian--.

Signed and Sealed this

Twenty-eighth Day of November, 2006

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 22
<212> TYPE: DNA
<213> ORGANISM: artificial sequence
<220> FEATURE:
```

-continued

<223> OTHER INFORMATION: Primer used for the PCR amplification of
m-rigui2 from KIAA 0347 sequence in the GenBank data base
(Accession No: AB002345).

<400> SEQUENCE: 1
gcaggaagat gtggacatga gc 22

<210> SEQ ID NO 2
<211> LENGTH: 24
<212> TYPE: DNA
<213> ORGANISM: artificial sequence
<220> FEATURE:
<223> OTHER INFORMATION: Primer used for the PCR amplification of
m-rigui2 from KIAA 0347 sequence in the GenBank data base
(Accession No: AB002345).

<400> SEQUENCE: 2
ggtcagagat gtacaccatc ttcc 24

<210> SEQ ID NO 3
<211> LENGTH: 1257
<212> TYPE: PRT
<213> ORGANISM: Mus musculus
<220> FEATURE:
<223> OTHER INFORMATION: m-rigui2 predicted amino acid s
equence.> SEQUENCE: 3

Met Asn Gly Tyr Val Asp Phe Ser Pro Ser Pro Thr Ser Pro Thr
5 10 15

Lys Glu Pro Gly Ala Pro Gln Pro Thr Gln Ala Val Leu Gln Glu
20 25 30

Asp Val Asp Met Ser Ser Gly Ser Ser Gly Asn Glu Asn Cys Ser
35 40 45

Thr Gly Arg Asp Ser Gln Gly Ser Asp Cys Asp Asp Asn Gly Lys
50 55 60

Glu Leu Arg Met Leu Val Glu Ser Ser Asn Thr His Pro Ser Pro
65 70 75

Asp Asp Ala Phe Arg Leu Met Met Thr Glu Ala Glu His Asn Pro
80 85 90

Ser Thr Ser Gly Cys Ser Ser Glu Gln Ser Ala Lys Ala Asp Ala
95 100 105

His Lys Glu Leu Ile Arg Thr Leu Lys Glu Leu Lys Val His Leu
110 115 120

Pro Ala Asp Lys Lys Ala Lys Gly Lys Ala Ser Thr Leu Ala Thr
125 130 135

Leu Lys Tyr Ala Leu Arg Ser Val Lys Gln Val Lys Ala Asn Glu
140 145 150

Glu Tyr Tyr Gln Leu Leu Met Ser Ser Glu Ser Gln Pro Cys Ser
155 160 165

Val Asp Val Pro Ser Tyr Ser Met Glu Gln Val Glu Gly Ile Thr
170 175 180

Ser Glu Tyr Ile Val Lys Asn Ala Asp Met Phe Ala Val Ala Val
185 190 195

Ser Leu Val Ser Gly Lys Ile Leu Tyr Ile Ser Asn Gln Val Ala
200 205 210

Ser Ile Phe His Cys Lys Lys Asp Ala Phe Ser Asp Ala Lys Phe
215 220 225

Val Glu Phe Leu Ala Pro His Asp Val Ser Val Phe His Ser Tyr
230 235 240

-continued

```
Thr Thr Pro Tyr Lys Leu Pro Pro Trp Ser Val Cys Ser Gly Leu
                245                 250                 255

Asp Ser Phe Thr Gln Glu Cys Met Glu Glu Lys Ser Phe Phe Cys
                260                 265                 270

Arg Val Ser Val Gly Lys His His Glu Asn Glu Ile Arg Tyr Gln
                275                 280                 285

Pro Phe Arg Met Thr Pro Tyr Leu Val Lys Val Gln Glu Gln Gln
                290                 295                 300

Gly Ala Glu Ser Gln Leu Cys Cys Leu Leu Leu Ala Glu Arg Val
                305                 310                 315

His Ser Gly Tyr Glu Ala Pro Arg Ile Pro Pro Glu Lys Arg Ile
                320                 325                 330

Phe Thr Thr Thr His Thr Pro Asn Cys Leu Phe Gln Ala Val Asp
                335                 340                 345

Glu Arg Ala Val Pro Leu Leu Gly Tyr Leu Pro Gln Asp Leu Ile
                350                 355                 360

Glu Thr Pro Val Leu Val Gln Leu His Pro Ser Asp Arg Pro Leu
                365                 370                 375

Met Leu Ala Ile His Lys Lys Ile Leu Gln Ala Gly Gly Gln Pro
                380                 385                 390

Phe Asp Tyr Ser Pro Ile Arg Phe Arg Thr Arg Asn Gly Glu Tyr
                395                 400                 405

Ile Thr Leu Asp Thr Ser Trp Ser Ser Phe Ile Asn Pro Trp Ser
                410                 415                 420

Arg Lys Ile Ser Phe Ile Ile Gly Arg His Lys Val Arg Val Gly
                425                 430                 435

Pro Leu Asn Glu Asp Val Phe Ala Ala Pro Pro Cys Pro Glu Glu
                440                 445                 450

Lys Thr Pro His Pro Ser Val Gln Glu Leu Thr Glu Gln Ile His
                455                 460                 465

Arg Leu Leu Met Gln Pro Val Pro His Ser Gly Ser Ser Gly Tyr
                470                 475                 480

Gly Ser Leu Gly Ser Asn Gly Ser His Glu His Leu Met Ser Gln
                485                 490                 495

Thr Ser Ser Ser Asp Ser Asn Gly Gln Glu Glu Ser His Arg Arg
                500                 505                 510

Arg Ser Gly Ile Phe Lys Thr Ser Gly Lys Ile Gln Thr Lys Ser
                515                 520                 525

His Val Ser His Glu Ser Gly Gly Gln Lys Glu Ala Ser Val Ala
                530                 535                 540

Glu Met Gln Ser Ser Pro Pro Ala Gln Val Lys Ala Val Thr Thr
                545                 550                 555

Ile Glu Arg Asp Ser Ser Gly Ala Ser Leu Pro Lys Ala Ser Phe
                560                 565                 570

Pro Glu Glu Leu Ala Tyr Lys Asn Gln Pro Pro Cys Ser Tyr Gln
                575                 580                 585

Gln Ile Ser Cys Leu Asp Ser Val Ile Arg Tyr Leu Glu Ser Cys
                590                 595                 600

Ser Glu Ala Ala Thr Leu Lys Arg Lys Cys Glu Phe Pro Ala Asn
                605                 610                 615

Ile Pro Ser Arg Lys Ala Thr Val Ser Pro Gly Leu His Ser Gly
                620                 625                 630

Glu Ala Ala Arg Pro Ser Lys Val Thr Ser His Thr Glu Val Ser
```

-continued

```
                635                 640                 645

Ala His Leu Ser Ser Leu Thr Leu Pro Gly Lys Ala Glu Ser Val
                650                 655                 660

Val Ser Leu Thr Ser Gln Cys Ser Tyr Ser Ser Thr Ile Val His
                665                 670                 675

Val Gly Asp Lys Lys Pro Gln Pro Glu Leu Glu Thr Val Glu Asp
                680                 685                 690

Met Ala Ser Gly Pro Glu Ser Leu Asp Gly Ala Ala Gly Gly Leu
                695                 700                 705

Ser Gln Glu Lys Gly Pro Leu Gln Lys Leu Gly Leu Thr Lys Glu
                710                 715                 720

Val Leu Ala Ala His Thr Gln Lys Glu Glu Gln Gly Phe Leu Gln
                725                 730                 735

Arg Phe Arg Glu Val Ser Arg Leu Ser Ala Leu Gln Ala His Cys
                740                 745                 750

Gln Asn Tyr Leu Gln Glu Arg Ser Arg Ala Gln Ala Ser Asp Arg
                755                 760                 765

Gly Leu Arg Asn Thr Ser Gly Leu Glu Ser Ser Trp Lys Lys Thr
                770                 775                 780

Gly Lys Asn Arg Lys Leu Lys Ser Lys Arg Val Lys Thr Arg Asp
                785                 790                 795

Ser Ser Glu Ser Thr Gly Ser Gly Gly Pro Val Ser His Arg Pro
                800                 805                 810

Pro Leu Met Gly Leu Asn Ala Thr Ala Trp Ser Pro Ser Asp Thr
                815                 820                 825

Ser Gln Ser Ser Cys Pro Ser Ala Pro Phe Pro Thr Ala Val Pro
                830                 835                 840

Ala Tyr Pro Leu Pro Val Phe Gln Ala Pro Gly Ile Val Ser Thr
                845                 850                 855

Pro Gly Thr Val Val Ala Pro Pro Ala Ala Thr His Thr Gly Phe
                860                 865                 870

Thr Met Pro Val Val Pro Met Gly Thr Gln Pro Glu Phe Ala Val
                875                 880                 885

Gln Pro Leu Pro Phe Ala Ala Pro Leu Ala Pro Val Met Ala Phe
                890                 895                 900

Met Leu Pro Ser Tyr Pro Phe Pro Pro Ala Thr Pro Asn Leu Pro
                905                 910                 915

Gln Ala Phe Leu Pro Ser Gln Pro His Phe Pro Ala His Pro Thr
                920                 925                 930

Leu Ala Ser Glu Ile Thr Pro Ala Ser Gln Ala Glu Phe Pro Ser
                935                 940                 945

Arg Thr Ser Thr Leu Arg Gln Pro Cys Ala Cys Pro Val Thr Pro
                950                 955                 960

Pro Ala Gly Thr Val Ala Leu Gly Arg Ala Ser Pro Pro Leu Phe
                965                 970                 975

Gln Ser Arg Gly Ser Ser Pro Leu Gln Leu Asn Leu Leu Gln Leu
                980                 985                 990

Glu Glu Ala Pro Glu Gly Ser Thr Gly Ala Ala Gly Thr Leu Gly
                995                 1000                1005

Thr Thr Gly Thr Ala Ala Ser Gly Leu Asp Cys Thr Ser Gly Thr
                1010                1015                1020

Ser Arg Asp Arg Gln Pro Lys Ala Pro Pro Thr Cys Asn Glu Pro
                1025                1030                1035
```

-continued

Ser Asp Thr Gln Asn Ser Asp Ala Ile Ser Thr Ser Ser Asp Leu
1040 1045 1050

Leu Asn Leu Leu Leu Gly Glu Asp Leu Cys Ser Ala Thr Gly Ser
1055 1060 1065

Ala Leu Ser Arg Ser Gly Ala Ser Ala Thr Ser Asp Ser Leu Gly
1070 1075 1080

Ser Ser Ser Leu Gly Phe Gly Thr Ser Gln Ser Gly Ala Gly Ser
1085 1090 1095

Ser Asp Thr Ser His Thr Ser Lys Tyr Phe Gly Ser Ile Asp Ser
1090 1095 1110

Ser Glu Asn Asn His Lys Ala Lys Met Ile Pro Asp Thr Glu Glu
1115 1120 1125

Ser Glu Gln Phe Ile Lys Tyr Val Leu Gln Asp Pro Ile Trp Leu
1130 1135 1140

Leu Met Ala Asn Thr Asp Asp Ser Ile Met Met Thr Tyr Gln Leu
1145 1150 1155

Pro Ser Arg Asp Leu Gln Ala Val Leu Lys Glu Asp Gln Glu Lys
1160 1165 1170

Leu Lys Leu Leu Gln Arg Ser Gln Pro Arg Phe Thr Glu Gly Gln
1175 1180 1185

Arg Arg Glu Leu Arg Glu Val His Pro Trp Val His Thr Gly Gly
1190 1195 1200

Leu Pro Thr Ala Ile Asp Val Thr Gly Cys Val Tyr Cys Glu Ser
1205 1210 1215

Glu Glu Lys Gly Asn Ile Cys Leu Pro Tyr Glu Glu Asp Ser Pro
1220 1225 1230

Ser Pro Gly Leu Cys Asp Thr Ser Glu Ala Lys Glu Glu Glu Gly
1235 1240 1245

Glu Gln Leu Thr Gly Pro Arg Ile Glu Ala Gln Thr
1250 1255

<210> SEQ ID NO 4
<211> LENGTH: 5816
<212> TYPE: DNA
<213> ORGANISM: Mus musculus
<220> FEATURE:
<221> NAME/KEY: CDS
<222> LOCATION: 145..3918
<223> OTHER INFORMATION: m-rigui2 cDNA Sequence

<400> SEQUENCE: 4
cgggagggcg acgcggcggc agcggcgcta ctgggactag cggctccggg cggctgcggc 60
gcaggccgag cgcaccaagt gacgggccga gcaagggaca gacgcgcggg ttgacgcggc 120
gaagcgctta ttccagagcc cgacatgaat ggatacgtgg acttctcccc aagtcccacc 180
agtcccacca aggagccagg ggcacctcag cccacccagg ctgtgctcca ggaagacgtg 240
gacatgagca gtggctccag cggaaacgag aactgctcca cgggacggga ctctcagggc 300
agtgactgcg acgacaatgg gaaggagctg cggatgctcg tggaatcttc caacactcac 360
cccagccctg atgatgcctt cagactcatg atgacagagg cagagcacaa cccctccacg 420
agcggctgca gtagtgagca gtctgccaaa gctgacgcac acaaagaact gataaggacc 480
ctgaaggagc tgaaggtcca cctccctgca gacaagaagg ccaaggggaa ggccagcacg 540
ctggcaaccc tgaagtatgc cctgcggagc gtgaagcagg tgaaggctaa tgaggagtac 600
taccagctgc taatgtccag tgagagccag ccctgcagtg tggatgtgcc ttcctacagc 660

-continued

```
atggagcagg ttgagggcat tacctccgag tatatcgtga agaacgcgga tatgtttgct    720
gtggctgtgt ccctggtttc tgggaagatc ctgtacatct ctaaccaagt ggcctccatc    780
tttcactgta agaaggacgc cttcagtgat gccaagtttg tggagttcct ggctcctcat    840
gacgtcagtg tgttccacag ctacaccacc ccttacaagc ttccgccctg gagtgtgtgc    900
agcggcttag attctttcac tcaggagtgc atggaggaga aatctttttt ctgccgtgtc    960
agtgttggga aacaccacga gaatgagatt cgctaccagc ccttccgcat gacaccctac   1020
ctggtcaagg tgcaagagca gcagggtgct gagagccagc tctgctgcct gctgctggca   1080
gagagggtac actcgggcta tgaagcgcct agaatccctc ctgagaagag gatcttcaca   1140
acaacccaca caccaaactg cttgttccag gctgtggatg aaagggcggt ccccctcctg   1200
ggctatctac ctcaggatct gatcgagacg cctgtgctcg tgcagctcca ccccagcgac   1260
cggcccttga tgctcgccat ccacaagaag atcctacagg ccggtggaca gcctttcgat   1320
tattctccca ttcgattccg cacccgcaac ggggagtaca tcacactgga cactagctgg   1380
tccagcttca tcaacccgtg gagcaggaag atatctttca tcattgggag gcacaaagtc   1440
agggtaggcc ctttgaatga ggatgtgttc gcagctcccc cgtgcccaga ggagaagact   1500
ccgcacccca gcgttcagga gctcacagaa caaatccacc ggctactgat gcagcctgtc   1560
ccccacagcg gctccagtgg ctatgggagc ctgggcagta acggatccca cgaacacctc   1620
atgagccaga catcatccag cgacagcaat ggccaagagg agtctcaccg gaggagatcc   1680
ggaattttta aaaccagtgg caagattcaa accaaaagtc acgtttctca tgagtctgga   1740
ggacagaagg aagcatctgt tgcagaaatg caaagcagcc ccccagctca ggtgaaagct   1800
gtcaccacca tagaaaggga cagctcaggg gccagcctac ccaaggccag cttcccagag   1860
gaactagcct ataagaacca gcctccttgc tcctaccagc agatcagctg cctggacagt   1920
gtcatcaggt acctggagag ctgcagcgag gcagccaccc tgaaaaggaa gtgcgagttc   1980
ccagccaaca tcccatcccg gaaggccaca gtcagccccg ggctgcactc tggagaggca   2040
gcgcggccct ccaaggtgac cagccacaca gaggtcagtg ctcacctgag ctccctgacg   2100
ctgccaggca aggccgagag tgtggtgtcc ctcaccagcc agtgcagcta cagcagcacc   2160
atcgtgcatg tgggcgacaa aaagccacag cccgagctag agacggtaga agatatggcc   2220
agtgggcccg agtccctgga tggtgcggcc ggcggcctca gccaagaaaa ggggcctctt   2280
cagaagttgg gcctcaccaa ggaagttctg gctgcacata cacagaaaga ggagcagggc   2340
ttcctgcaga ggttcaggga ggtgagcagg ctcagtgccc tgcaggctca ctgccagaac   2400
tatctccagg agcggtcccg agcccaggcg agtgatcgag gactaagaaa tacttctgga   2460
ctagagtcat cttggaaaaa aactggaaag aacaggaaac tgaagtcaaa acgcgtcaag   2520
actcgggact cttctgagag cacagggtct ggaggaccag tgtcccaccg acctcccctc   2580
atgggcctga atgccacagc ctggtcaccc tccgacacat cccagtccag ctgcccctct   2640
gcacccttcc ccaccgcagt gccagcttac cccctacctg tgttccaggc acccggaata   2700
gtatccacac cagggacggt ggtggcgcca cctgcagcca ccccacactgg cttcaccatg   2760
cctgttgtgc ctatgggcac ccagcctgaa ttcgcagtgc agcccctgcc attcgctgcc   2820
cctttggctc ctgtcatggc cttcatgctg cccagctacc cgttcccacc agcaacccca   2880
aacctgcctc aggccttcct ccccagccag cctcactttc cagcccaccc cacacttgcc   2940
tccgaaataa ctcctgcctc ccaggctgag ttccctagtc ggacctcgac gctcagacag   3000
```

-continued

```
ccgtgcgctt gcccagtcac ccctccagcc ggcacagtgg ccctgggcag agcctcccca   3060

ccgctcttcc agtccagagg cagtagtccc ctacaactta acctgcttca gctagaggag   3120

gcgcctgaag gcagcactgg agccgcaggg accctgggga ccacagggac agcagcttct   3180

ggtctggact gcacatctgg cacatctcgg gatcggcagc caaaggcacc tccaacatgc   3240

aacgagccct cagacactca gaacagtgat gccatctcca cgtcaagtga cctgctcaac   3300

ctccttctgg gcgaggacct ctgctcggcc actggctcag ccctgtctag aagcggggca   3360

tccgccacct cagactctct gggctccagc tcgctgggct tcggcacatc ccaaagtggg   3420

gcaggcagta gtgacacaag tcacaccagc aaatactttg gaagcattga ctcttcagag   3480

aataatcaca aagcaaaaat gatcccagac acggaggaaa gcgagcagtt cattaagtac   3540

gtcttgcagg accccatctg gctgctgatg gccaacacag acgacagcat catgatgaca   3600

taccagctgc cctcccggga tctccaggcg gtgttgaagg aggaccagga gaagctgaag   3660

ctgctgcaga ggtcccagcc ccggttcaca gagggccaga ggcgagagct ccgagaggtt   3720

catccgtggg tccacactgg gggcctgcct acggccatcg atgtgacagg ctgtgtttac   3780

tgcgagagtg aggagaaagg caacatttgc ctgccatatg aggaagacag tccttccccg   3840

ggactctgtg atacctcaga agccaaagag gaggaaggtg aacagctgac aggccccagg   3900

atagaggccc agacgtaacc ctgtccccca gccagaggtc gacattagac ggtgctcgga   3960

agaaggggga agatcttgtg gtttctaatc acatggaccc atacctacac tgcttttttt   4020

gttttaggaa aaacaaaaaa caaaaacacc atagttttct ggcggtggaa caaaactgag   4080

gggaggttta ggaggaaatc catttttgta ttaaaataga aatacggaat ttgggggatg   4140

gggtgagatt cgtcattgaa cttgagactg aggtggtctg tgttgtcatg gaggctgcct   4200

catggtcctc aggagtgtct tgacctccat gaaacctctt tccagtgtgc caatgtcctc   4260

tggcccctgt ggattgttct gaaacataac accaggatgt ggcaggtaac agggaagcca   4320

caagaggcta tccaccaagg gcccagcttt ctggaacttt ctcacagtgt gattgtatct   4380

cccaagcaga gagaccatct ctcctgacat cctctcagtg tgttccctta cgtggtttgg   4440

agcatggtgt agcagctttg gcttcaggtc ctgcctgtgg tggtcaacat tccagtctga   4500

catggcttct gttcgtcaac aaagttgaaa tgcctgctct ggactagtgg agctcagtgg   4560

cttctgcaaa cgatgcccac catcagacta gcacccccac actgtacatt tctctgctgt   4620

tcttgtatcc tttttagacc attgtggcca gtgtgcagag agagctgtgg catcatcagc   4680

catgttgccg tgtctgcatg gtggcctctg caagccaggc tttgttgctg tagaggacac   4740

cgtcacgtgt ttgttctttg gttggactct ctcagacatt agctcccagc agaaagcagc   4800

cactgagcac ggaggagaga ggcacccaca ctgctgccct gagttctcca gtttgcaggg   4860

agctcagcct cccactctat atgtatatac tcctagctac tgtggcttcg ggtctctgtc   4920

acatctatct gtgctgctgg tcctcagatc actggaacct gtggagagaa ggggacctct   4980

ctgcccagct ctacaaaact ttatgctgca tcagacatcc aaagattgtt ccgacatgct   5040

tgcgggtgac ccctggtgga acgagacatc accagtgagg aatcattgga cttaaaagta   5100

gacaaagcct ggagcagagg aagctgtttc ctgagtctga agtggctact ggggacatgt   5160

cctgctgtag ttggttttca tggtaaagcc atctgaggcc tgaatattac ccctattttt   5220

cataaacaca agaactctat tttttttatt aaagcaacac cacctttcac agtgatcagg   5280

tagtagccat gttttaaagg aaattcaatg ttacagacag ctgcctctct gaccagtctg   5340

atcctaaggg tagatagaag atggtctaag cctacgcttg ttacttaaac acaaaactgc   5400
```

-continued

```
caaaaccttc tctcttctct cttgaatgtt taccatcagc gttattttat gattatttaa   5460

tatatagtcc ttgattgtta actgctaaga agttgacttc ctaggataat tttgtgaatc   5520

tgtttacaag atgccaagca tccagccctg ttttctttag aatgtgtgct tacacgggtg   5580

tcctaagaca ttctctattt taaactgagc cttcttttta atgtaaataa gctctcagag   5640

tttgtgcgat gatgattcgt gagccttgcc ggacaagagg tttgttcatg cgcaaaccaa   5700

acgtaccttc acccagtgca atatatttgt gtgactgctt gtgtcttttt atgacttttt   5760

tgccttttag aaaattgtta aataaagcaa gtatattttt attttcaaaa aaaaaa       5816
```

<210> SEQ ID NO 5
<211> LENGTH: 1291
<212> TYPE: PRT
<213> ORGANISM: Mus musculus
<220> FEATURE:
<223> OTHER INFORMATION: m-rigui1

<400> SEQUENCE: 5

```
Met Ser Gly Pro Leu Glu Gly Ala Asp Gly Gly Gly Asp Pro Arg
                5                   10                  15

Pro Gly Glu Pro Phe Cys Pro Gly Gly Val Pro Ser Pro Gly Ala
                20                  25                  30

Pro Gln His Arg Pro Cys Pro Gly Pro Ser Leu Ala Asp Asp Thr
                35                  40                  45

Asp Ala Asn Ser Asn Gly Ser Ser Gly Asn Glu Ser Asn Gly Pro
                50                  55                  60

Glu Ser Arg Gly Ala Ser Gln Arg Ser Ser His Ser Ser Ser Ser
                65                  70                  75

Gly Asn Gly Lys Asp Ser Ala Leu Leu Glu Thr Thr Glu Ser Ser
                80                  85                  90

Lys Ser Thr Asn Ser Gln Ser Pro Ser Pro Pro Ser Ser Ser Ile
                95                  100                 105

Ala Tyr Ser Leu Leu Ser Ala Ser Ser Glu Gln Asp Asn Pro Ser
                110                 115                 120

Thr Ser Gly Cys Ser Ser Glu Gln Ser Ala Arg Ala Arg Thr Gln
                125                 130                 135

Lys Glu Leu Met Thr Ala Leu Arg Glu Leu Lys Leu Arg Leu Pro
                140                 145                 150

Pro Glu Arg Arg Gly Lys Gly Arg Ser Gly Thr Leu Ala Thr Leu
                155                 160                 165

Gln Tyr Ala Leu Ala Cys Val Lys Gln Val Gln Ala Asn Gln Glu
                170                 175                 180

Tyr Tyr Gln Gln Trp Ser Leu Glu Glu Gly Glu Pro Cys Ala Met
                185                 190                 195

Asp Met Ser Thr Tyr Thr Leu Glu Glu Leu Glu His Ile Thr Ser
                200                 205                 210

Glu Tyr Thr Leu Arg Asn Gln Asp Thr Phe Ser Val Ala Val Ser
                215                 220                 225

Phe Leu Thr Gly Arg Ile Val Tyr Ile Ser Glu Gln Ala Gly Val
                230                 235                 240

Leu Leu Arg Cys Lys Arg Asp Val Phe Arg Gly Ala Arg Phe Ser
                245                 250                 255

Glu Leu Leu Ala Pro Gln Asp Val Gly Val Phe Tyr Gly Ser Thr
                260                 265                 270
```

-continued

```
Thr Pro Ser Arg Leu Pro Thr Trp Gly Thr Gly Thr Ser Ala Gly
                275                 280                 285

Ser Gly Leu Lys Asp Phe Thr Gln Glu Lys Ser Val Phe Cys Arg
                290                 295                 300

Ile Arg Gly Gly Pro Asp Arg Asp Pro Gly Pro Arg Tyr Gln Pro
                305                 310                 315

Phe Arg Leu Thr Pro Tyr Val Thr Lys Ile Arg Val Ser Asp Gly
                320                 325                 330

Ala Pro Ala Gln Pro Cys Cys Leu Leu Ile Ala Glu Arg Ile His
                335                 340                 345

Ser Gly Tyr Glu Ala Pro Arg Ile Pro Pro Asp Lys Arg Ile Phe
                350                 355                 360

Thr Thr Arg His Thr Pro Ser Cys Leu Phe Gln Asp Val Asp Glu
                365                 370                 375

Arg Ala Ala Pro Leu Leu Gly Tyr Leu Pro Gln Asp Leu Leu Gly
                380                 385                 390

Ala Pro Val Leu Leu Phe Leu His Pro Glu Asp Arg Pro Leu Met
                395                 400                 405

Leu Ala Ile His Lys Lys Ile Leu Gln Leu Ala Gly Gln Pro Phe
                410                 415                 420

Asp His Ser Pro Ile Arg Phe Cys Ala Arg Asn Gly Glu Tyr Val
                425                 430                 435

Thr Met Asp Thr Ser Trp Ala Gly Phe Val His Pro Trp Ser Arg
                440                 445                 450

Lys Val Ala Phe Val Leu Gly Arg His Lys Val Arg Thr Ala Pro
                455                 460                 465

Leu Asn Glu Asp Val Phe Thr Pro Pro Ala Pro Ser Pro Ala Pro
                470                 475                 480

Ser Leu Asp Ser Asp Ile Gln Glu Leu Ser Glu Gln Ile His Arg
                485                 490                 495

Leu Leu Leu Gln Pro Val His Ser Ser Ser Pro Thr Gly Leu Cys
                500                 505                 510

Gly Val Gly Pro Leu Met Ser Pro Gly Pro Leu His Ser Pro Gly
                515                 520                 525

Ser Ser Ser Asp Ser Asn Gly Gly Asp Ala Glu Gly Pro Gly Pro
                530                 535                 540

Pro Ala Pro Val Thr Phe Gln Gln Ile Cys Lys Asp Val His Leu
                545                 550                 555

Val Lys His Gln Gly Gln Gln Leu Phe Ile Glu Ser Arg Ala Lys
                560                 565                 570

Pro Pro Pro Arg Pro Arg Leu Leu Ala Thr Gly Thr Phe Lys Ala
                575                 580                 585

Lys Val Leu Pro Cys Gln Ser Pro Asn Pro Glu Leu Glu Val Ala
                590                 595                 600

Pro Val Pro Asp Gln Ala Ser Leu Ala Leu Ala Pro Glu Glu Pro
                605                 610                 615

Glu Arg Lys Glu Thr Ser Gly Cys Ser Tyr Gln Gln Ile Asn Cys
                620                 625                 630

Leu Asp Ser Ile Leu Arg Tyr Leu Glu Ser Cys Asn Ile Pro Ser
                635                 640                 645

Thr Thr Lys Arg Lys Cys Ala Ser Ser Ser Ser Tyr Thr Ala Ser
                650                 655                 660

Ser Ala Ser Asp Asp Asp Lys Gln Arg Ala Gly Pro Val Pro Val
```

-continued

```
                665                 670                 675

Gly Ala Lys Lys Asp Pro Ser Ser Ala Met Leu Ser Gly Glu Gly
                680                 685                 690

Ala Thr Pro Arg Lys Glu Pro Val Val Gly Gly Thr Leu Ser Pro
                695                 700                 705

Leu Ala Leu Ala Asn Lys Ala Glu Ser Val Val Ser Val Thr Ser
                710                 715                 720

Gln Cys Ser Phe Ser Ser Thr Ile Val His Val Gly Asp Lys Lys
                725                 730                 735

Pro Pro Glu Ser Asp Ile Ile Met Met Glu Asp Leu Pro Gly Leu
                740                 745                 750

Ala Pro Gly Pro Ala Pro Ser Pro Ala Pro Ser Pro Thr Val Ala
                755                 760                 765

Pro Asp Pro Thr Pro Asp Ala Tyr Arg Pro Val Gly Leu Thr Lys
                770                 775                 780

Ala Val Leu Ser Leu His Thr Gln Lys Glu Glu Gln Ala Phe Leu
                785                 790                 795

Asn Arg Phe Arg Asp Leu Gly Arg Leu Arg Gly Leu Asp Thr Ser
                800                 805                 810

Ser Val Ala Pro Ser Ala Pro Gly Cys His His Gly Pro Ile Pro
                815                 820                 825

Pro Gly Arg Arg His His Cys Arg Ser Lys Ala Lys Arg Ser Arg
                830                 835                 840

His His His His Gln Thr Pro Arg Pro Glu Thr Pro Cys Tyr Val
                845                 850                 855

Ser His Pro Ser Pro Val Pro Ser Ser Gly Pro Trp Pro Pro Pro
                860                 865                 870

Pro Ala Thr Thr Pro Phe Pro Ala Met Val Gln Pro Tyr Pro Leu
                875                 880                 885

Pro Val Phe Ser Pro Arg Gly Gly Pro Gln Pro Leu Pro Pro Ala
                890                 895                 900

Pro Thr Ser Val Ser Pro Ala Thr Phe Pro Ser Pro Leu Val Thr
                905                 910                 915

Pro Met Val Ala Leu Val Leu Pro Asn Tyr Leu Phe Pro Thr Pro
                920                 925                 930

Pro Ser Tyr Pro Tyr Gly Val Ser Gln Ala Pro Val Glu Gly Pro
                935                 940                 945

Pro Thr Pro Ala Ser His Ser Pro Ser Pro Ser Leu Pro Pro Pro
                950                 955                 960

Pro Leu Ser Pro Pro His Arg Pro Asp Ser Pro Leu Phe Asn Ser
                965                 970                 975

Arg Cys Ser Ser Pro Leu Gln Leu Asn Leu Leu Gln Leu Glu Glu
                980                 985                 990

Ser Pro Arg Thr Glu Gly Gly Ala Ala Ala Gly Gly Pro Gly Ser
                995                 1000                1005

Ser Ala Gly Pro Leu Pro Pro Ser Glu Glu Thr Ala Glu Pro Glu
                1010                1015                1020

Ala Arg Leu Val Glu Val Thr Glu Ser Ser Asn Gln Asp Ala Leu
                1025                1030                1035

Ser Gly Ser Ser Asp Leu Leu Glu Leu Leu Leu Gln Glu Asp Ser
                1040                1045                1050

Arg Ser Gly Thr Gly Ser Ala Ala Ser Gly Ser Leu Gly Ser Gly
                1055                1060                1065
```

-continued

```
Leu Gly Ser Gly Ser Gly Ser Gly Ser His Glu Gly Gly Ser Thr
                1070                1075                1080

Ser Ala Ser Ile Thr Arg Ser Ser Gln Ser Ser His Thr Ser Lys
                1085                1090                1095

Tyr Phe Gly Ser Ile Asp Ser Ser Glu Ala Glu Ala Gly Ala Ala
                1100                1105                1110

Arg Ala Arg Thr Glu Pro Gly Asp Gln Val Ile Lys Cys Val Leu
                1115                1120                1125

Gln Asp Pro Ile Trp Leu Leu Met Ala Asn Ala Asp Gln Arg Val
                1130                1135                1140

Met Met Thr Tyr Gln Val Pro Ser Arg Asp Ala Ala Ser Val Leu
                1145                1150                1155

Lys Gln Asp Arg Glu Arg Leu Arg Ala Met Gln Lys Gln Gln Pro
                1160                1165                1170

Arg Phe Ser Glu Asp Gln Arg Arg Glu Leu Gly Ala Val His Ser
                1175                1180                1185

Trp Val Arg Lys Gly Gln Leu Pro Arg Ala Leu Asp Val Met Ala
                1190                1195                1200

Cys Val Asp Cys Gly Ser Ser Val Gln Asp Pro Gly His Ser Asp
                1205                1210                1215

Asp Pro Leu Phe Ser Glu Leu Asp Gly Leu Gly Leu Glu Pro Met
                1220                1225                1230

Glu Glu Gly Gly Gly Glu Gly Gly Gly Cys Gly Val Gly Gly Gly
                1235                1240                1245

Gly Gly Asp Gly Gly Glu Glu Ala Gln Thr Gln Ile Gly Ala Lys
                1250                1255                1260

Gly Ser Ser Ser Gln Asp Ser Ala Met Glu Glu Glu Glu Gln Gly
                1265                1270                1275

Gly Gly Ser Ser Ser Pro Ala Leu Pro Ala Glu Glu Asn Ser Thr
                1280                1285                1290

Ser
```